(12) United States Patent  
Jawidzik et al.

(10) Patent No.: US 9,149,591 B2  
(45) Date of Patent: Oct. 6, 2015

(54) VALVE ASSEMBLY FOR CONTROLLING THE FLOW RATE OF A FLUID

(71) Applicant: Mindray DS USA, Inc., Mahwah, NJ (US)

(72) Inventors: Geoffrey C. Jawidzik, Mahwah, NJ (US); Xiong Zhibin, Shenzhen (CN); Chen Peitao, Shenzhen (CN); Wang Gongmin, Shenzhen (CN); Cai Kun, Shenzhen (CN)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 283 days.

(21) Appl. No.: 13/677,154

(22) Filed: Nov. 14, 2012

(65) Prior Publication Data

US 2014/0130882 A1    May 15, 2014

(51) Int. Cl.
| | |
|---|---|
| *F16K 11/22* | (2006.01) |
| *F16K 31/44* | (2006.01) |
| *F16K 31/528* | (2006.01) |
| *A61M 16/01* | (2006.01) |
| *A61M 16/12* | (2006.01) |
| *A61M 16/20* | (2006.01) |
| *F16K 31/60* | (2006.01) |

(52) U.S. Cl.
CPC ............ *A61M 16/01* (2013.01); *A61M 16/12* (2013.01); *A61M 16/203* (2014.02); *F16K 31/60* (2013.01); *A61M 2202/0208* (2013.01); *A61M 2202/0283* (2013.01); *A61M 2205/106* (2013.01); *A61M 2205/16* (2013.01); *A61M 2205/276* (2013.01); *A61M 2205/505* (2013.01); *Y10T 137/0368* (2015.04); *Y10T 137/7761* (2015.04)

(58) Field of Classification Search
CPC ............................. A16K 31/60; A61M 16/203
USPC ........................ 251/266, 267, 268; 137/606
See application file for complete search history.

(56) References Cited

U.S. PATENT DOCUMENTS

| | | | | |
|---|---|---|---|---|
| 957,592 | A * | 5/1910 | Allen ............................ | 251/266 |
| 1,024,884 | A * | 4/1912 | Fitz et al. ...................... | 251/265 |
| 1,151,776 | A * | 8/1915 | Fuller .......................... | 251/266 |
| 1,360,340 | A * | 11/1920 | Wetzler ........................ | 137/306 |
| 1,495,964 | A * | 5/1924 | Reid ......................... | 137/630.18 |
| 3,367,365 | A * | 2/1968 | Stevens ......................... | 137/553 |
| 3,390,943 | A * | 7/1968 | Myers .............................. | 431/78 |
| 3,503,586 | A * | 3/1970 | Bordes .......................... | 251/266 |
| 4,721,131 | A * | 1/1988 | Ciordinik et al. ............. | 137/554 |
| 4,759,386 | A * | 7/1988 | Grouw, III .................... | 137/554 |
| 6,024,087 | A | 2/2000 | Kersey et al. | |
| 2009/0071554 | A1* | 3/2009 | Beckman et al. ............. | 137/554 |

* cited by examiner

*Primary Examiner* — Marina Tietjen  
*Assistant Examiner* — Seth W Mackay-Smith  
(74) *Attorney, Agent, or Firm* — Kory D. Christensen; Stoel Rives LLP

(57) ABSTRACT

In various embodiments, an electronic flow selector of a fluid flow control system may be used to select a flow rate of a fluid. The fluid flow control system may be operated in an electronic mode and a manual mode. When the system is in a manual mode, mechanical backup flow selectors may be used to select the flow rate of a fluid. The mechanical backup flow selectors may include a position detection system to determine the flow rate of a fluid. Flow selectors of the flow control system may be rotationally engaged with the valve shafts of each needle valve, while allowing them to translate axially. The flow selectors may remain axially fixed while the valve shafts are axially translated with respect to the needle valves in a fluid flow control system.

25 Claims, 25 Drawing Sheets

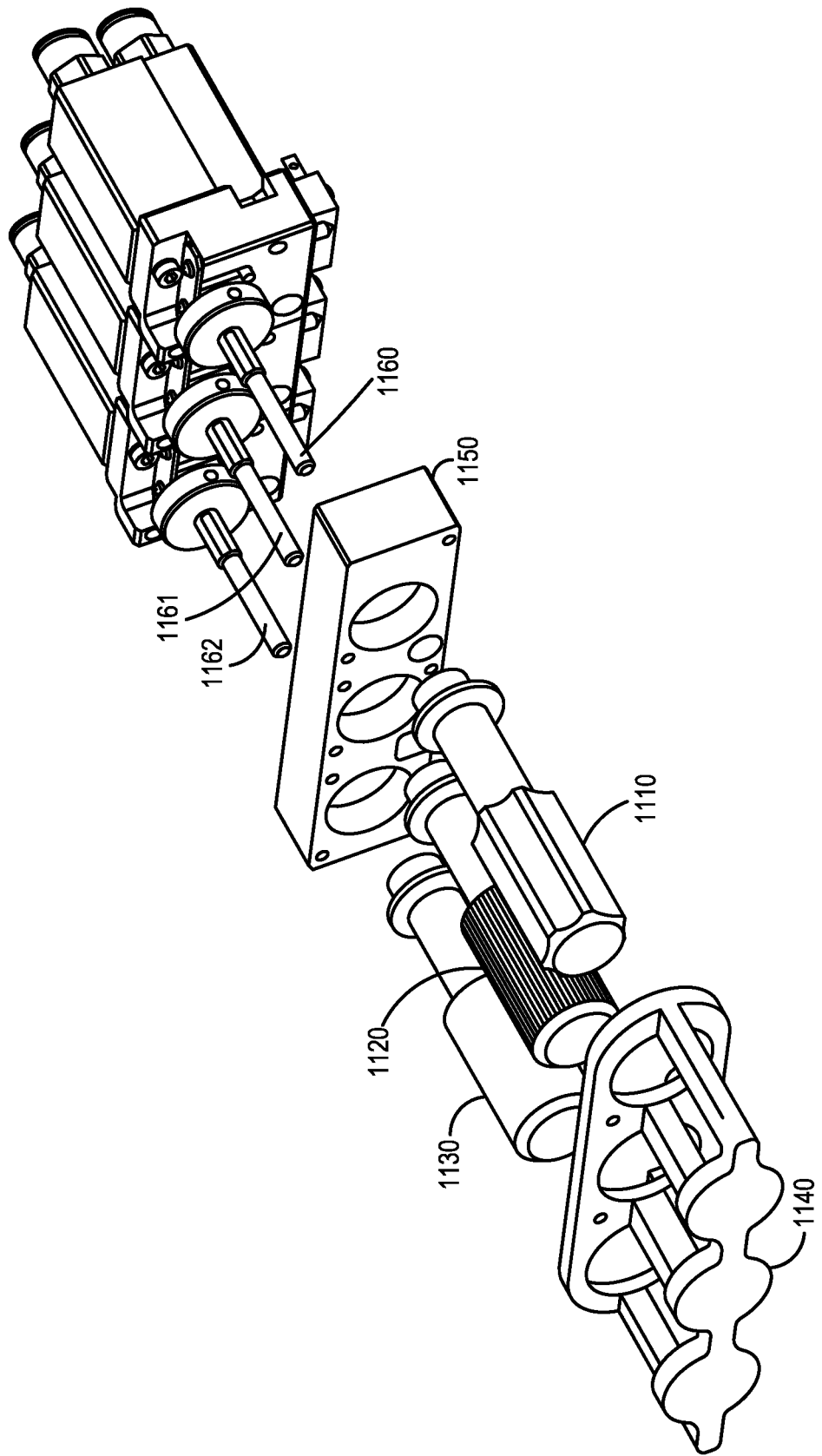

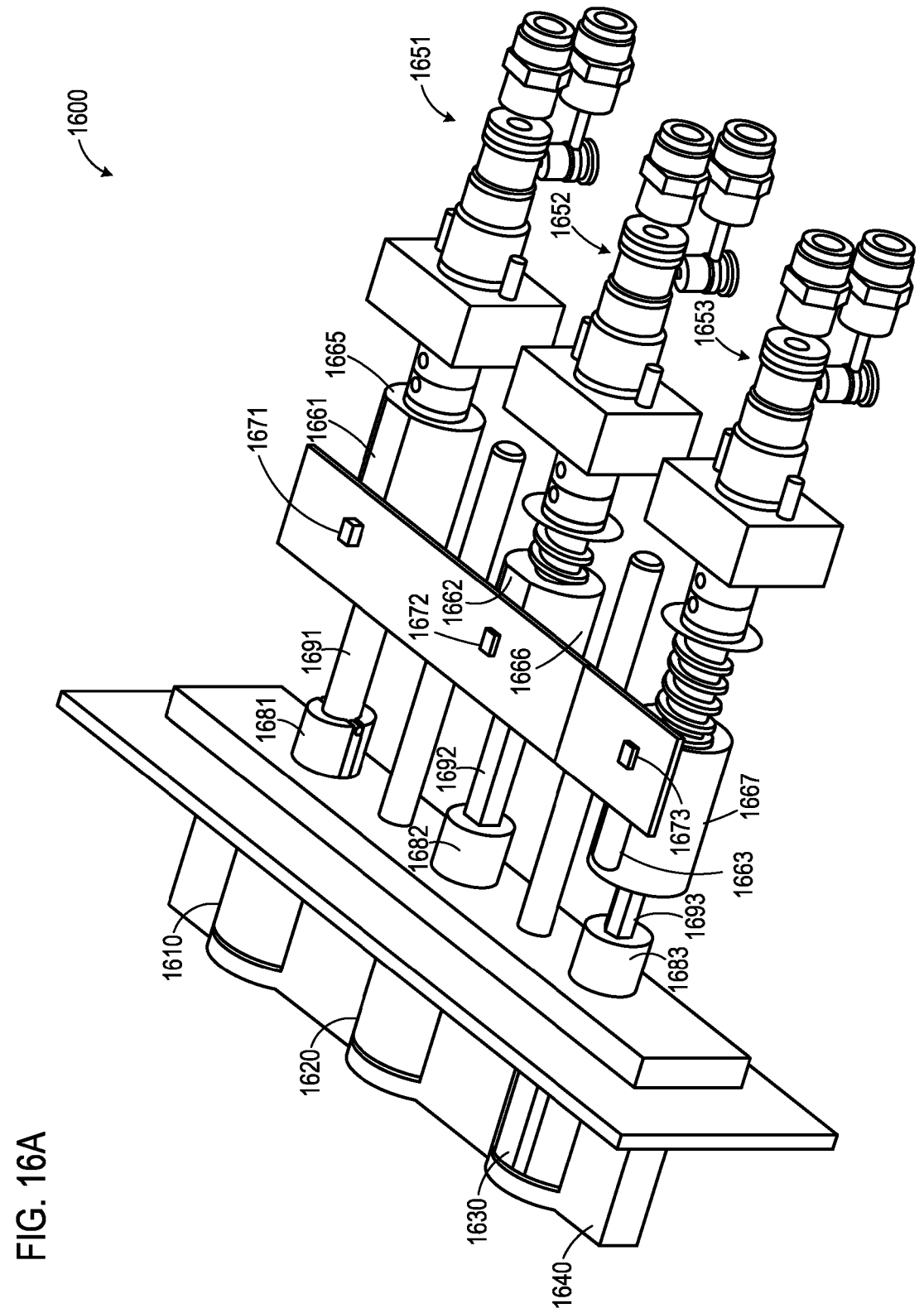

VALVE ASSEMBLY FOR CONTROLLING THE FLOW RATE OF A FLUID

TECHNICAL FIELD

This disclosure relates generally to controlling the flow of fluids via valve assembly. Particularly, this disclosure relates to flow selectors configured to remain axially fixed relative to a rotating valve shaft and valve position detection systems.

SUMMARY

In various instances, the rates of flow of fresh gases, such as oxygen, nitrous oxide, and air, in modern anesthesia delivery systems may be controlled by a practitioner either electronically or mechanically. In various embodiments, one or more rotatable flow selectors, such as control knobs, may be configured to electronically control a flow rate of a gas when in a powered state. The anesthesia delivery system may also include mechanical backup controls for controlling the flow rate of one or more of the gases when in an unpowered state. In one embodiment, a three-way selector valve and/or a combination of normally-open valves and normally-closed valves may be used to selectively enable the flow of gas from either electronically controlled electronic proportional valves or mechanically operated needle valves. The valve assemblies, flow selectors, and position detection systems may be utilized with or without variation in any of a wide variety of flow control systems.

In various embodiments, when a fluid flow control system is in a powered state, a three-way selector valve, or other diversion valve system, may allow fluid from the electronically controlled electronic proportional valves to be delivered to a patient. When the fluid flow control system is in an unpowered state or a manual override is selected, the three-way selector valve may allow fluid from the mechanically controlled needle valves to be delivered to a patient. Alternatively, a diversion valve system may include a combination of normally-open and normally-closed valves instead of or in addition to a three-way selector valve, as described herein. In some embodiments, the diversion valve system may be located between a fluid supply and a fluid control valve. In other embodiments, the diversion valve system may be located between a fluid control valve and a fluid output.

An electronic flow control valve may be configured to selectively receive a fluid from a fluid supply. An electronic flow selector may allow a practitioner to select a flow rate of the first fluid via the electronic control valve. For example, an encoder may electronically encode a selection made via the electronic flow selector and transmit the encoded selection to an electronic controller. The electronic controller may transmit a control signal to the electronic flow control valve to control the flow rate of the fluid based on the selection made via the electronic flow selector. The electronic flow control valve may include an electronic proportional valve and the electronic flow selector may include a rotary knob configured to be manually rotated by a practitioner. Alternatively, the electronic flow selector may include any of a wide variety of digital and/or analog selectors.

In some embodiments, a unique electronic flow control valve may be used to control the flow rate of each available fluid. A unique electronic flow selector may be available to control the flow rate of each of the electronic flow control valves. Alternatively, one or more of the electronic flow selectors may be selectively assignable to control two or more electronic flow control valves. For example, a system may include three electronic flow control valves, one for oxygen, one for air, and one for nitrous oxide. The system may incorporate only two electronic flow selectors, one of which may be selectively used to control either the flow rate of the air or the flow rate of the nitrous oxide. Any electronic flow selector may be permanently assigned or selectively assigned to control the flow rate of any one or more of the available fluids.

One or more mechanical flow control valves may be configured to control the flow rate of each of the available fluids. For example, a unique needle valve may be used to mechanically control the flow rate of each available fluid. A manual flow selector, such as a knob or slider, may be actuated by a practitioner to mechanically adjust the flow rate through each of the needle valves. In some embodiments, the manual flow selectors may be disabled and/or retracted to prevent adjustments when the system is in a powered state.

In some embodiments, the rotatable valve shaft of a needle valve may engage an engagement cavity in a rotatable flow selector, such as a knob. The rotatable flow selector may be configured to remain in a fixed position axially with respect to the valve housing. The engagement cavity of the rotatable flow selector may be configured to receive an end of the valve shaft. When the rotatable flow selector is rotated, the valve shaft may rotate as well. The valve shaft may translate axially to increase or decrease the flow rate of the fluid. In various embodiments, the valve shaft is also configured to translate within the engagement cavity. Accordingly, the flow selector may remain in a fixed position axially with respect to the valve housing, while still remaining rotatably engaged with the valve shaft.

The engagement cavity and valve shaft may be any non-circular shape, such that the valve shaft remains rotationally engaged while still free to axially translate. For example, the engagement cavity and valve shaft may be hexagonal or include engaging protrusions/intrusions. The engagement cavity and valve shaft may be elliptical, square, hexagonal, circular with intrusions/protrusions, and/or any n-sided polygonal shape or other non-circular form.

In a powered state, one or more electronic flow selectors may be adjusted to control the flow rate of one or more fluids through one or more electronic flow control valves. In the powered state, backup manual flow control valves may be disabled and/or otherwise prevented from supplying a fluid or combination of fluids. Moreover, in the powered state, manual flow selectors associated with the backup manual flow control valves may be disabled and/or retracted to prevent adjustments.

In an unpowered state, or when a manual override selection is made, the electronic flow control valves may be disabled and/or otherwise prevented from supplying a fluid or combination of fluids. Manual flow selectors may be enabled and/or deployed to allow a practitioner to manually control a flow rate of one or more fluids through the backup manual flow control valves.

A position indicator associated with the axial translation of a valve shaft relative to a flow channel may be configured to provide an indication of the position of the valve shaft. The position indicator may indicate, based on the position of the valve shaft relative to a flow channel, the currently selected flow rate. The valve assembly may include a position detector configured to interface with the position indicator to detect the flow rate based on the relative position of the valve shaft. For example, the position detector may determine when the valve shaft is translated such that the flow rate of the fluid is at a particular flow rate, above a threshold flow rate, below a threshold flow rate, at a maximum, and/or zero.

In some embodiments, the position detector and/or position indicator may be configured to provide an indication of the current flow rate (e.g., any flow rate between zero and the maximum flow rate) or only when a particular flow rate is reached (e.g., a home state of flow, a maximum flow rate, and/or a zero flow rate). The position indicator may include one or more protrusions and/or intrusions on the valve shaft configured to actuate a position detector when the valve shaft is axially translated to a predetermined location. The protrusions and/or intrusions may be formed on an axially-floating bushing on the valve shaft.

In some embodiments, the position indicator may include a valve stop plunger connected to the valve shaft, such that valve stop plunger actuates a position detector when the valve shaft is axially translated to a predetermined location. The valve stop plunger may translate axially in conjunction with axial translations of the valve shaft. Alternatively, the valve stop plunger may be actuated by a cam configured to rotate in response to a rotation of the valve shaft. The cam may move the valve stop plunger relative to the position detector based on the relative axial location of the valve shaft with respect to the flow channel in a valve assembly.

In some embodiments, when the manual flow selectors are retracted, such as upon power restoration or a reset of the system, the flow rate of each of the backup manual flow control valves may be reset to a home state, in which a predetermined flow rate of a gas will automatically flow when the system enters an unpowered state.

In one embodiment, the electronic flow control valve may comprise an electronically controlled stepper motor configured to adjust the flow rate of a fluid through a mechanical flow control valve, such as a needle valve. In various examples provided herein, the fluid is described as a gas, such as oxygen, nitrous oxide, and/or air. However, any of a wide variety of liquids and/or gases may be used in conjunction with various embodiments of the systems and methods described herein.

BRIEF DESCRIPTION OF THE DRAWINGS

FIG. 11A illustrates an exploded view of a flow selector assembly and associated needle valves.

FIG. 16A illustrates a top view of a flow selector assembly and needle valves configured with axially-floating bushings, position indicators, and position detectors associated with the valve shafts.

DETAILED DESCRIPTION

Figure 1:
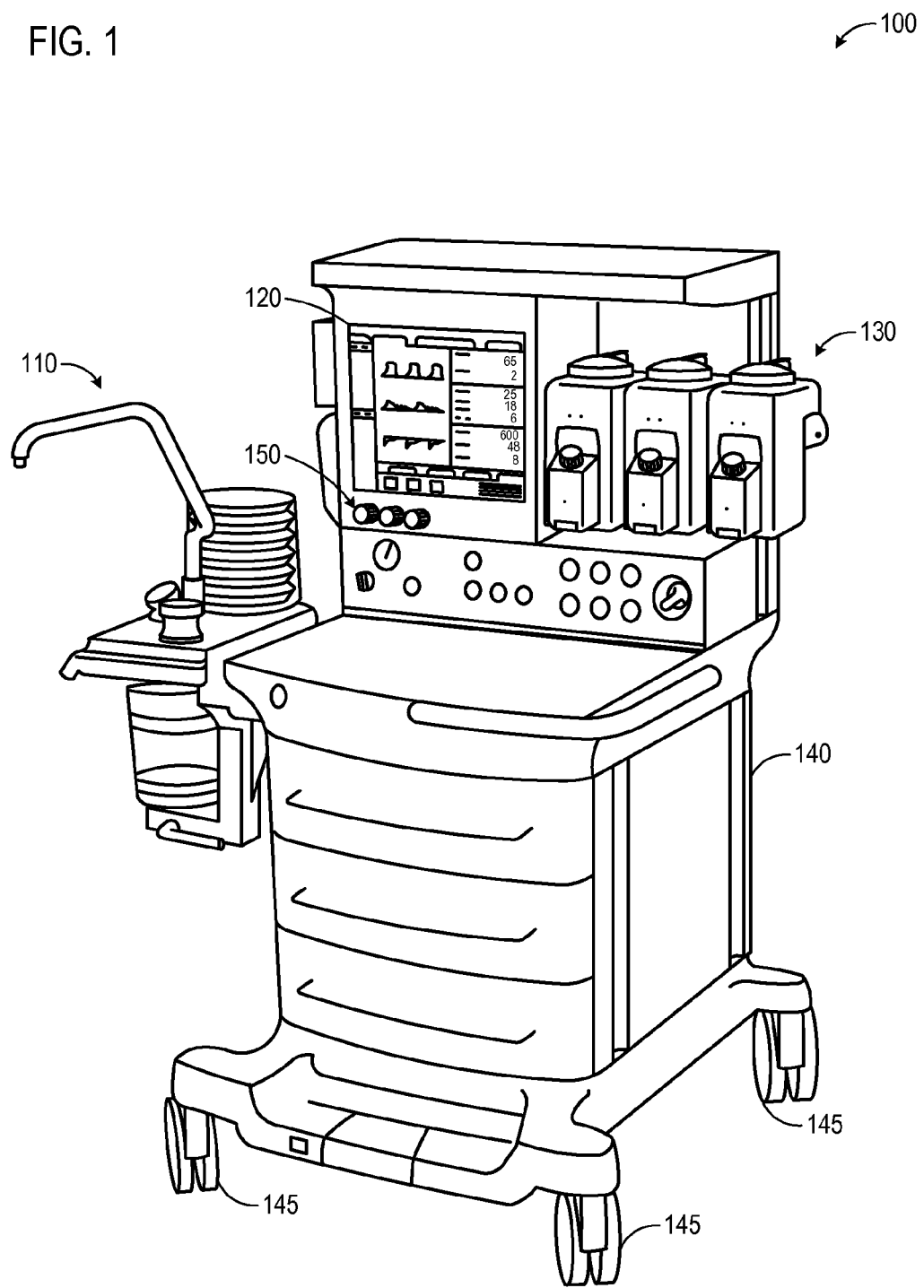
FIG. 1 illustrates an anesthesia delivery machine configured with three manual flow selectors, one each for controlling the flow of oxygen, nitrous oxide, and air.

While electronic flow control of gases may be useful during anesthesia delivery, it may be desirable to provide mechanical backup controls as well. For example, in the event of power loss, it may be desirable to continue supplying gases during anesthesia delivery. In some embodiments, electronic controls, such as trim knobs, used in conjunction with encoders, may facilitate the electronic adjustment of the flow rate of one or more gases during anesthesia delivery. Separate backup flow selectors (e.g., knobs) may be available for use in the event of power failure or power unavailability. In such embodiments, the practitioner may need to engage the backup knobs, switch the machine from an electronic mode to a manual mode, and/or ensure that the manual knobs are set to a desirable state prior to switching to a manual mode.

Power loss during anesthesia delivery may be confusing and/or disruptive during a critical medical procedure. It may be an inconvenience and/or confusing for a practitioner to see two sets of knobs for controlling the same set of gases. In various embodiments of the present disclosure, flow selectors, such as rotary knobs, may be electronically operable when a fluid flow control system is in a powered state and backup flow selectors may be retracted or otherwise disabled when a fluid flow control system is in a powered state. In an unpowered state, or when a practitioner engages the backup system, the backup flow selectors may be deployed or otherwise enabled.

The number of diversion valve systems, mechanically operated valves, electronically operated valves, controllers, encoders, flow selectors, and/or other components described herein may correspond to the number of gases (or liquids) available. In various anesthesia delivery systems, oxygen, nitrous oxide, and/or air may each be independently controllable and/or proportionally controllable. A mixture of one or more gases may be used in conjunction with a vaporizer to deliver anesthesia.

According to various embodiments, a user may select a flow rate of a combination of oxygen and air to be supplied to a patient. A user may also select a flow rate of nitrous oxide to be provided to a patient instead of air. In some embodiments, the nitrous oxide may be supplied in addition to air. Regardless of the selections made by a user, a safe amount of oxygen may be automatically supplied to the patient, as ensured by an oxygen ratio controller (ORC).

In one embodiment, a diversion valve system may direct the flow of a gas (or liquid) from a gas supply to either a mechanical flow control valve, such as a mechanically operated needle valve, or an electronic flow control valve, such as an electronic proportion valve, depending on whether or not the system has power or if a backup system has been engaged.

If the system is in a powered state, the selected flow rate may be encoded and transmitted to a controller. The controller may then send a control signal to the electronic proportion valve in order to achieve the selected flow rate. A deployment assembly may maintain the backup flow control valves in a retracted state. Alternatively, a deployment assembly may maintain the backup flow control valves in a disabled or non-functioning state.

If the system is in an unpowered state or a backup system is engaged by a practitioner, the backup flow selectors may be deployed, enabled, and/or otherwise caused to function. A selected flow rate may then be mechanically translated from a flow selector to a mechanically operated flow control valve, such as a needle valve, to achieve the selected flow rate.

According to various embodiments, the diversion valve system may include normally-open and normally-closed valves in order to selectively prevent the gas from flowing from (or to) both the mechanically operated needle valve and the electronic proportion valve. The diversion valve system may be implemented using any of a wide variety of valves and/or control systems, such as a three-way selector valve.

In some embodiments, the needle valve may be used as the mechanical flow control valve and the same needle valve in combination with the electronic stepper motor may be considered the electronic flow control valve. In various embodiments, the flow selector may comprise any of a wide variety of knobs, buttons, rotatable actuators, slides, and/or other analog and/or digital selection devices.

A rotatable flow selector may be configured to remain in a fixed position axially with respect to a valve housing. The engagement cavity of the rotatable flow selector may be configured to receive an end of the valve shaft. When the rotatable flow selector is rotated, the valve shaft may rotate. The valve shaft may translate axially to increase or decrease the flow rate of the fluid. In various embodiments, the valve shaft may translate within the engagement cavity. Accordingly, the flow selector may remain in a fixed position axially with respect to the valve housing, while still remaining rotatably engaged with the valve shaft.

A position indicator may indicate, based on the position of the valve shaft relative to a flow channel, the currently selected flow rate. In some embodiments, the position indicator, in conjunction with a position detector, may be configured to provide an indication of the current flow rate (e.g., any flow rate between zero and the maximum flow rate) or only when a particular flow rate is reached (e.g., a home state of flow, a maximum flow rate, and/or a zero flow rate).

In various embodiments, a controller or control system may be implemented as any combination of hardware, firmware, and/or software. For example, a controller may be implemented as a field-programmable gate array (FPGA). In some embodiments, an electronic controller for transmitting a control signal to an electronic flow control valve may be distinct from other electronic components in a gas flow control system, such as microprocessors and other electronic components associated with displays, touch screens, data storage, data connectivity, etc. The reliability of the electronic flow controls may be improved by separating the electronic flow controls from other electronic features of an anesthesia delivery device and/or by implementing it in hardware rather than software.

While the various examples and embodiments disclosed herein are described in conjunction with a gas flow control system, many of the embodiments could be used or modified for use with any type of fluid, including various gases and liquids. Gases used for anesthesia delivery, such as oxygen, nitrous oxide, and air, are used herein as examples of gases that can be controlled via the presently described fluid flow control systems and are referred to as gas flow control systems.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special purpose processing device, such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic, optical, flash memory, or other machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

In various embodiments, an anesthesia delivery system may be configured with electronic flow control and backup manual flow control valves for controlling the flow of oxygen, nitrous oxide, and air. When power is available, the anesthesia delivery system may utilize electronic flow control valves controlled by one or more electronic flow selectors. A practitioner may interact with the anesthesia delivery machine by providing inputs with regards to a flow of one or more gases. For instance, a practitioner may provide an input via an electronic flow selector. The electronic flow selector may comprise a mechanically rotatable knob and a rotary encoder.

When the anesthesia delivery system is in a powered state, the user may utilize an electronic mode or select a manual mode. When the anesthesia delivery system is in an unpowered state, the anesthesia delivery system may be used in a manual mode. In the electronic mode, the three source gases, oxygen, nitrous oxide, and air, may flow through the electronic flow control valves, an oxygen ratio controller, and/or check valves. In a manual mode, the three source gases may flow through backup manual flow control valves, an oxygen ratio controller, and/or a backpressure valve.

In various embodiments, a user may achieve a desired ratio of gases by starting with zero flow and sequentially adding source gases to the total flow, noting the effect of each on total flow rate. In an alternative embodiment, the user may achieve a desired ratio of gases by starting at a "home state" flow of oxygen and then adjust each of the gases to achieve the desired flow rate. The oxygen ratio controller may ensure a safe ratio of oxygen-to-nitrous oxide.

FIG. 1 illustrates an anesthesia delivery machine 100 configured with three manual flow selectors 150, one each for controlling the flow of oxygen, nitrous oxide, and air. The illustrated anesthesia delivery machine 100 may include a breathing system 110, anesthetic gas vaporizers 130, and/or other components of an anesthetic delivery system. The anesthesia delivery machine 100 may include a cart 140 and/or wheels 145 for portability. An electronic display 120 may provide information regarding the flow rate and/or anesthetic delivery process to a practitioner. Additionally, the electronic display 120 may be configured as a touch sensitive display to allow a practitioner to provide a selection of a flow rate.

Figure 2:
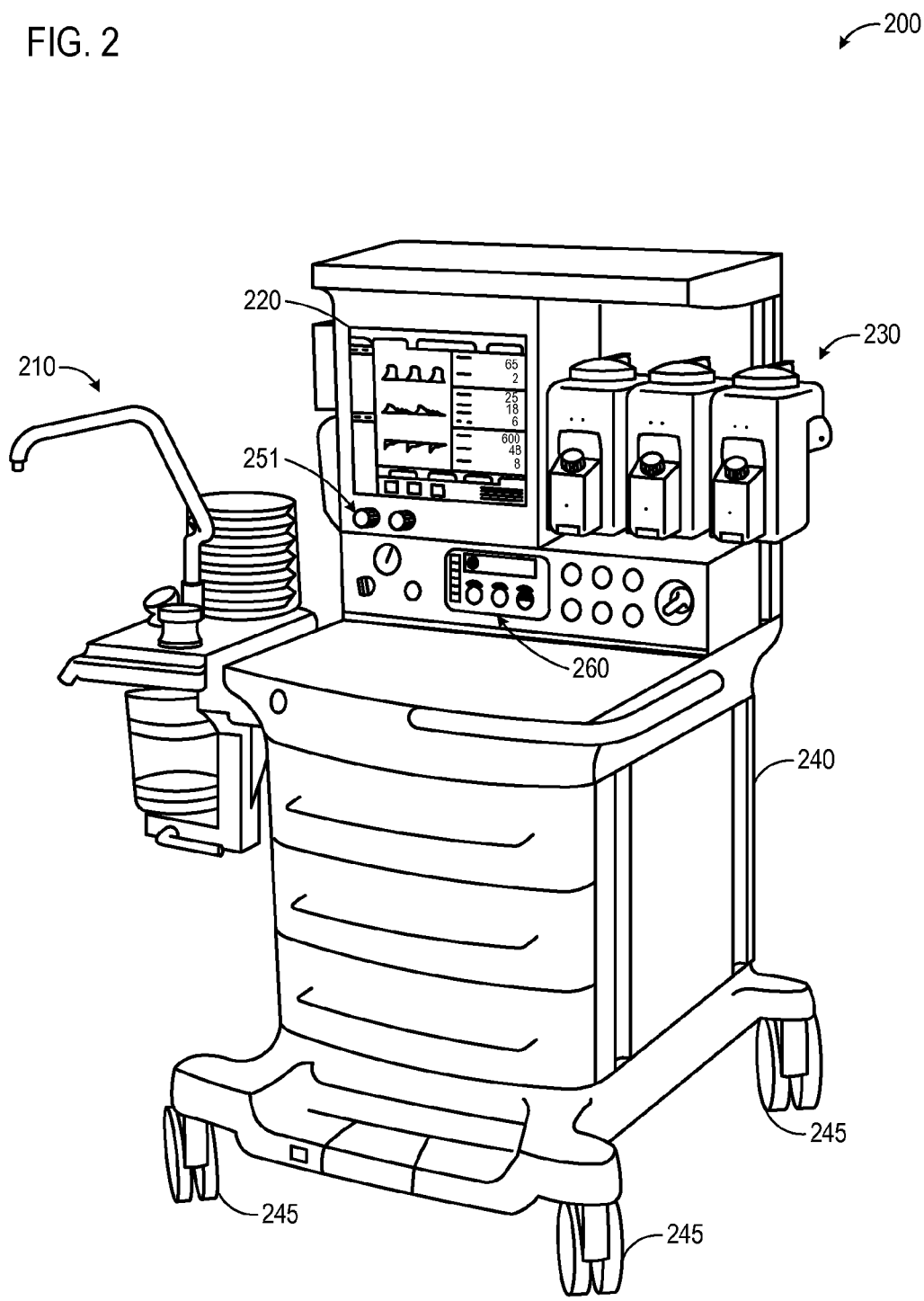
FIG. 2 illustrates an anesthesia delivery machine configured with two electronic flow selectors, configurable to selectively control each of the three gases, and three backup manual flow selectors, for controlling each of the three gases.

FIG. 2 illustrates an anesthesia delivery machine 200 configured with two electronic flow selectors 251, configurable to selectively control each of the three gases, and three backup manual flow selectors 260, for controlling each of the three gases. The anesthesia delivery machine 200 may include a breathing system 210, anesthetic gas vaporizers 230, and/or other components of an anesthetic delivery system. The anesthesia delivery machine 200 may include a cart 240 and/or wheels 245 for portability. An electronic display 220 may provide information regarding the flow rate and/or anesthetic delivery process to a practitioner. Additionally, the electronic display 220 may be configured as a touch sensitive display to allow a practitioner to provide a selection of a flow rate.

The three backup manual flow selectors 260 may remain retracted and/or disabled when the anesthesia delivery machine 200 is in an electronic mode. When the anesthesia delivery machine 200 enters a manual mode (e.g., due to power loss or a user selection), the three backup manual flow selectors 260 may be deployed, unlocked, and/or otherwise function. As previously described, various internal components, switches, normally-open valves, normally-closed valves, three-way valves, and/or other components may regulate the flow of gases within the anesthesia delivery machine 200 based on whether it is in a manual mode or an electronic mode.

Figure 3:
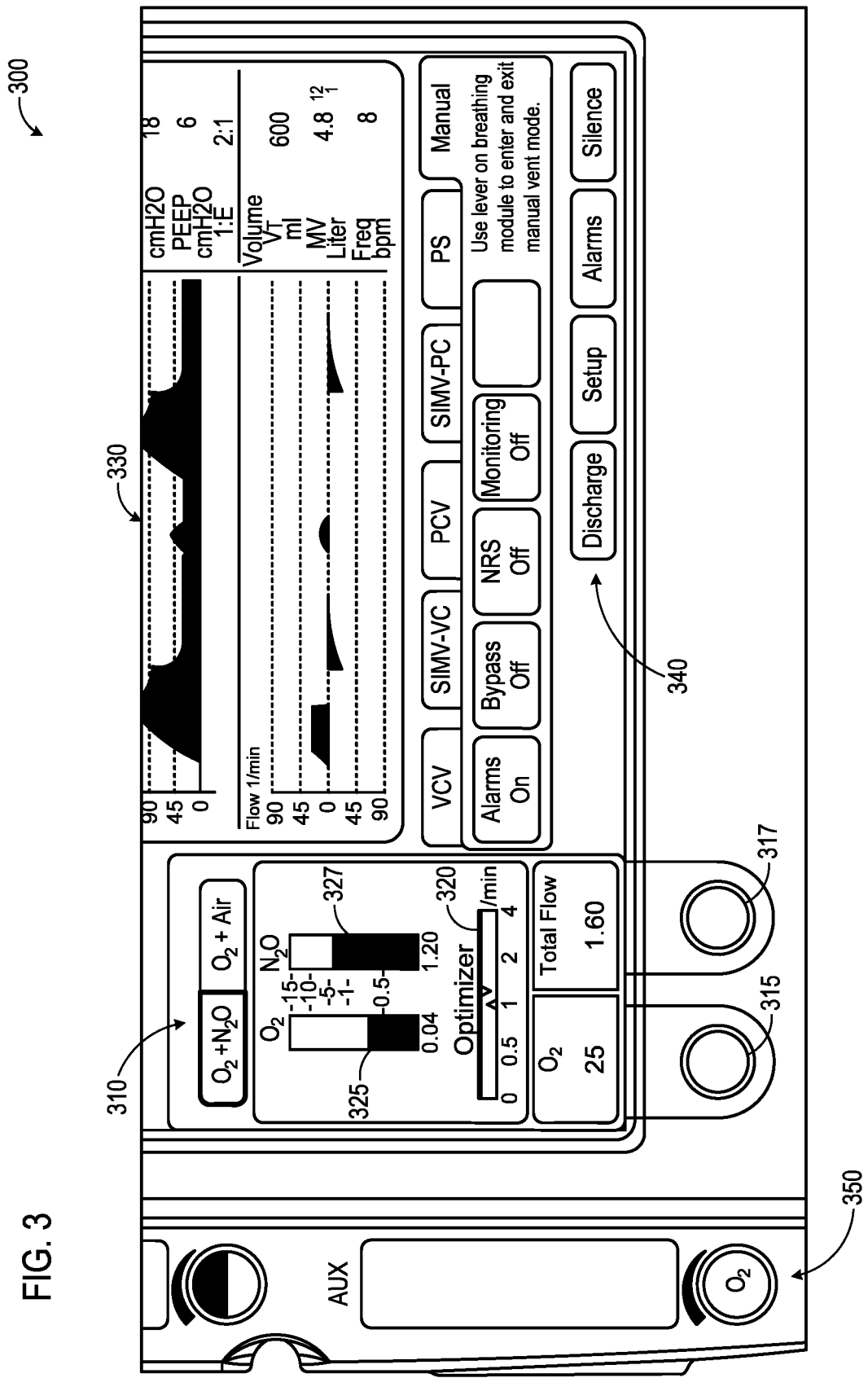
FIG. 3 illustrates a close-up view of a control panel of an anesthesia delivery machine, including two electronic flow selectors selectively configurable to control either oxygen and nitrous oxide, or oxygen and air.

FIG. 3 illustrates a close-up view of a control panel 300 of an anesthesia delivery machine, including two electronic flow selectors 315 and 317 selectively configurable to control either oxygen and nitrous oxide, or oxygen and air. As illustrated, the anesthesia delivery machine may include a panel 330 to display various telemetry data associated with a patient, information associated with the flow rate of gases, and/or information associated with the delivery of one or more anesthetics. Various inputs 340 may be available to change the display of panel 330 and/or to control the anesthesia delivery machine.

In a first position, a selection toggle 310 may allow a practitioner to control the flow rate of oxygen and nitrous oxide via the respective electronic flow selectors 315 and 317. In a second position, the selection toggle 310 may allow a practitioner to control the flow rate of oxygen and air via the respective flow selectors 315 and 317. Depending on the position of the selection toggle 310, various flow rate monitoring devices and ratio measuring devices 320, 325, and 327 may indicate the flow rate of one or more gases and/or combination of gases. In various embodiments, auxiliary inputs and outputs 350 for oxygen and/or another gas may be available.

While the illustrated embodiment shows two electronic flow selectors 315 and 317, any number of flow selectors and associated gases may be utilized. For example, a flow control system may be configured to allow for the electronic and backup manual control of one, two, three, four . . . or N number of gases or liquids. In some embodiments, more than one flow selector (e.g., knob, toggle, dial, slider, switch) may be configured to control the flow rate of the same gas. Additional selection toggles 310 and/or a multi-position selection toggle may be used to control the number of gases controlled by any number of corresponding flow control selection knobs. The flow selectors may include and/or utilize any analog or digital selection mechanism for selecting a flow rate, including knobs, as illustrated in the figures.

Figure 4:
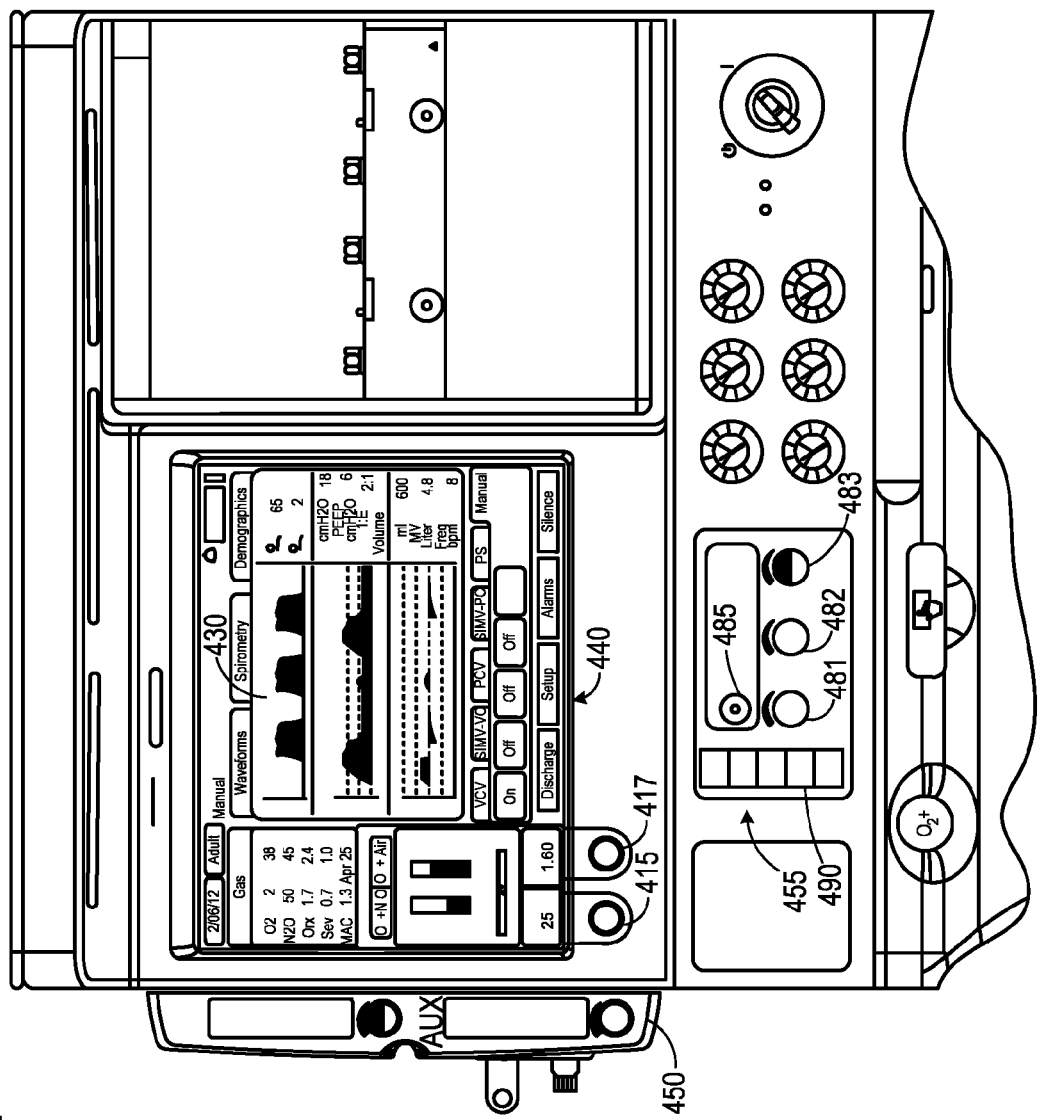
FIG. 4 illustrates a wider view of a control panel of an anesthesia delivery machine, including backup manual flow controls for controlling the flow of three gases independently.

FIG. 4 illustrates a wider view of a control panel 400 of an anesthesia delivery machine, including backup manual flow controls 481, 482, and 483 for controlling the flow of three gases independently. When the anesthesia delivery system is in a powered state and the user has not selected a manual mode, the anesthesia delivery system may be in an electronic mode. In an electronic mode, two electronic flow selectors 415 and 417 may be used to control either oxygen and nitrous oxide or oxygen and air, depending on the selection made via a selection toggle. An electronic display 430 may display information associated with the flow rate of one or more gases, an anesthetic, and/or patient telemetry data. Various touch inputs 440 may be available. An auxiliary control panel 450 may allow for one or more gases to be supplied to an auxiliary device.

When the anesthesia delivery system is in an unpowered state and/or the user has selected a manual mode, the anesthesia delivery system may be in a manual mode. In a manual mode, the flow rate of one or more gases and/or the amount of anesthetic delivery may be controlled via a manual panel 455. The electronic display 430, the touch inputs 440, the electronic flow selectors 415 and 417, and other electronic components may be unavailable in an unpowered state and one or more of them may be unavailable and/or otherwise disabled in a manual mode selected when in a powered state.

The manual panel 455 may include a total flow rate indicator 490, a manual mode selector 485 (e.g., a spring-loaded plunger), and one or more manually operated flow selectors 481, 482, and 483. According to various embodiments, a manually operated flow selector may be available for each available gas or for each available critical gas. In various embodiments, manually operated flow selectors 481, 482, and 483 may be disabled, retracted, locked, and/or otherwise not operational when the anesthesia delivery system is in an electronic mode. In a manual mode, the manually operated flow selectors 481, 482, and 483 may be enabled, deployed, unlocked, and/or otherwise become operational.

Figure 5:
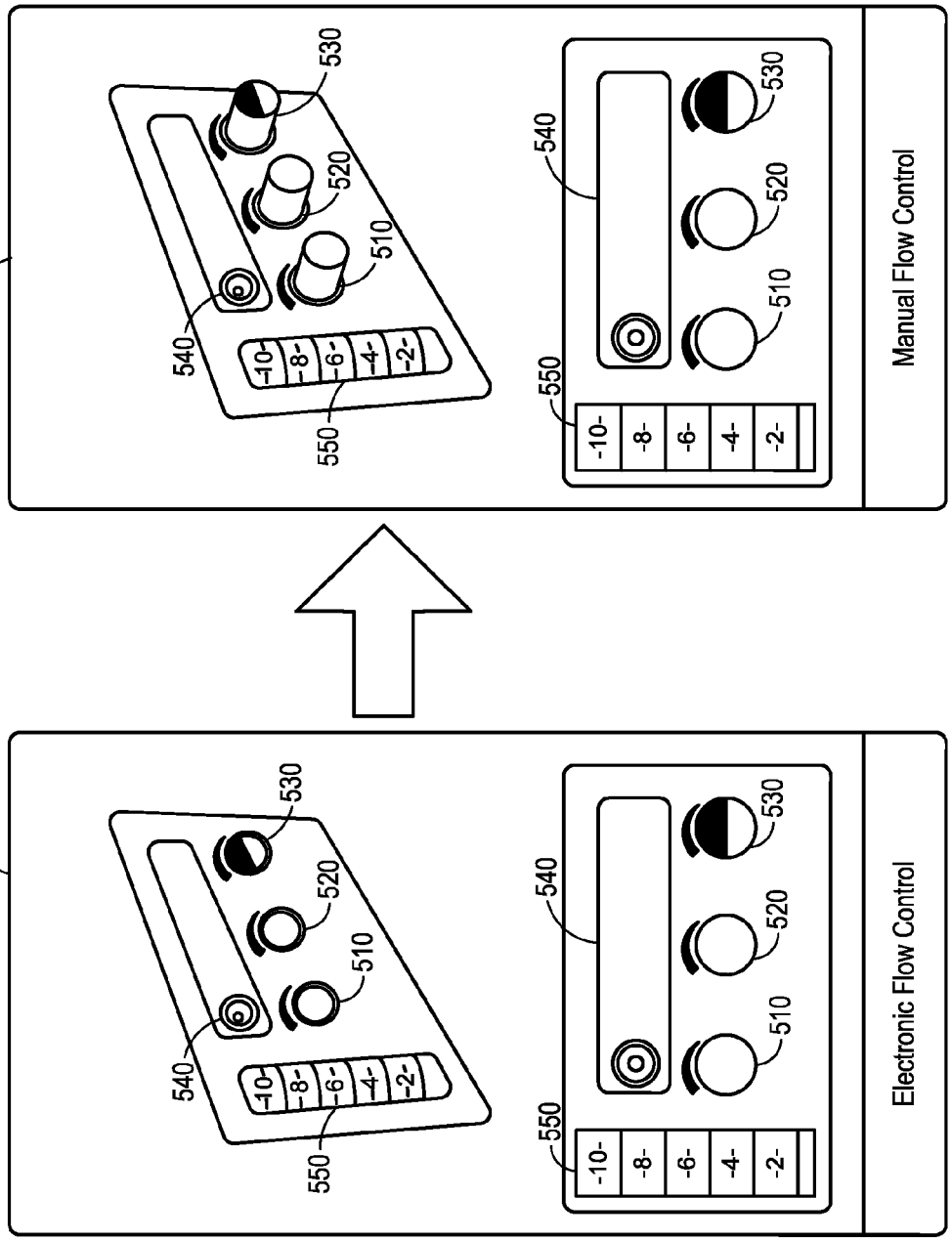
FIG. 5 illustrates an exemplary embodiment of backup manual flow selectors in a retracted state and the backup manual flow selectors in a deployed state.

FIG. 5 illustrates an exemplary embodiment 500 of backup manual flow selectors 510, 520, and 530 in a retracted state 501 and the backup manual flow selectors 510, 520, and 530 in a deployed state 502. The illustrated embodiment includes a perspective view (top of 501 and 502) and a front view (bottom of 501 and 502). As illustrated, a total flow indicator 550 may be available to indicate the flow rate of one or more gases. A manual mode selector 540 may allow a user to cause an anesthesia delivery system to enter a manual mode even when the system is in a powered state. The system may automatically enter a manual mode when the system transitions from a powered state to an unpowered state. In an electronic mode, the flow selectors 510, 520, and 530 may remain in a retracted state (501), so as to be unobtrusive, disabled, and/or otherwise not inconvenience or confuse a user. In a manual mode, the flow selectors 510, 520, and 530 may be deployed (502), so as to be more obtrusive, enabled, and/or otherwise alert a user that they may be used to control the flow rate of one or more gases.

In some embodiments, the default position of a manual flow selector may be above 0 liters per minute. For example, a default position for a manual flow selector associated with the flow rate of oxygen may have a home state of 2 liters per minute, so as to continue providing a critical gas (or liquid) to a patient even in the event the anesthesia delivery system loses power during use.

Figure 6:
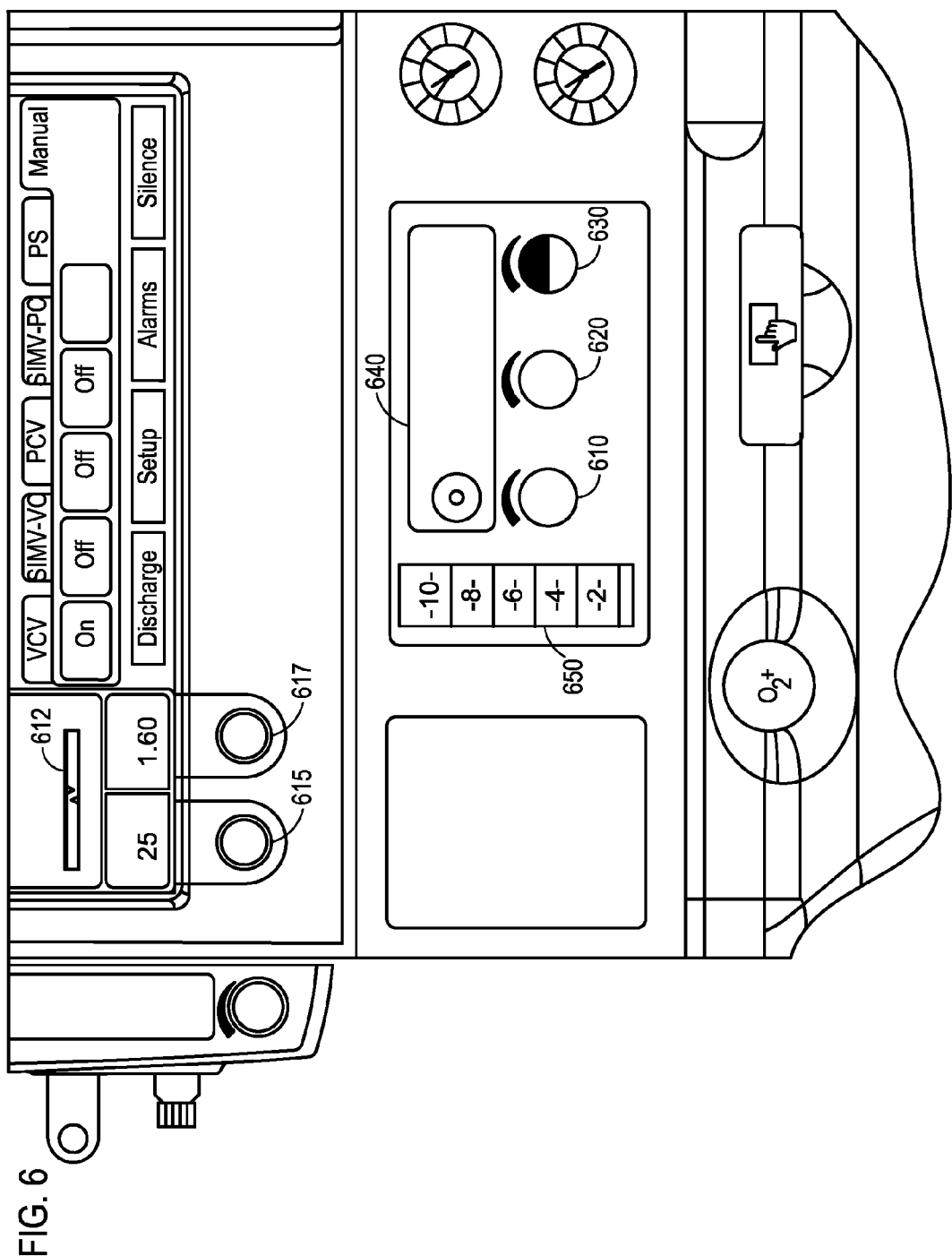
FIG. 6 illustrates another view of a control panel of an anesthesia delivery machine, including both electronic flow selectors and backup manual flow selectors.

FIG. 6 illustrates another view of a control panel of an anesthesia delivery machine that includes both electronic flow selectors 615 and 617 and backup manual flow selectors 610, 620, and 630. In an electronic mode, backup manual flow selectors 610, 620, and 630 may be retracted, locked, disengaged, and/or otherwise non-operational. The flow rate of two or more gases may be controlled by the electronic flow selectors 615 and 617. An optimizer indicator 612 may indicate a total flow rate of gases selected by the electronic flow selectors 615 and 617.

The anesthesia delivery system may enter a manual mode due to the loss of power and/or in response to a user selecting a manual mode selector 640. In one embodiment, the manual mode selector 640 may include a plunger configured to actuate a solenoid or motor to deploy the manual flow selectors 610, 620, and 630. In a manual mode, a flow rate indicator 650 may indicate the total flow rate of gases as selected by the backup manual flow selectors 610, 620, and 630.

Figure 7:
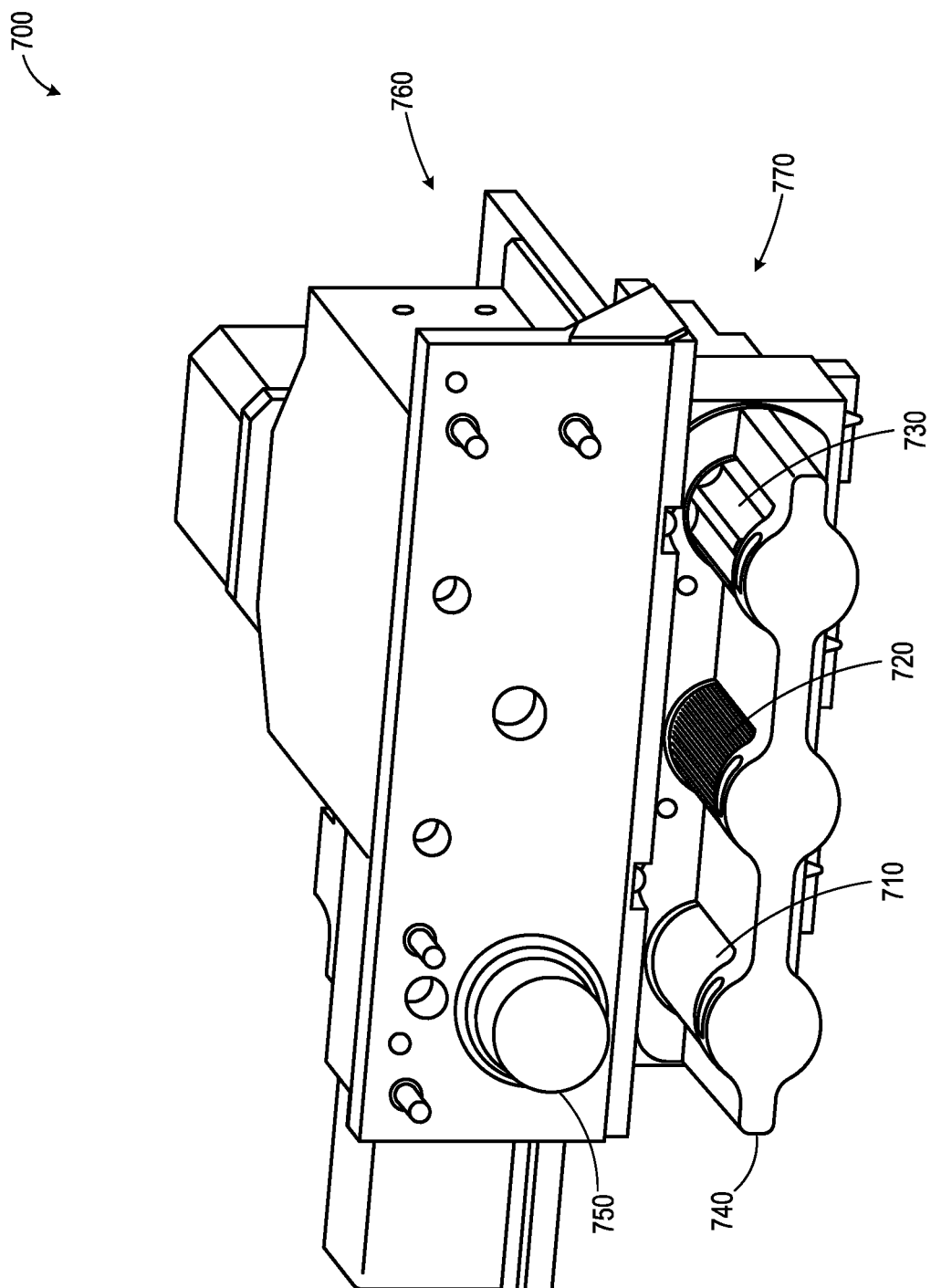
FIG. 7 illustrates a mechanical apparatus configured to selectively deploy and retract three manual flow selectors.

FIG. 7 illustrates a mechanical apparatus 700 configured to selectively deploy and retract three manual flow selectors 710, 720, and 730. According to various embodiments, the mechanical apparatus 700 may be mounted within a housing of an anesthesia delivery system and/or other fluid flow control system. The embodiments of the mechanical apparatus 700 and related embodiments are described herein in conjunction with an anesthesia delivery system and/or other fluid flow control system. However, the mechanical apparatus 700 could be utilized in conjunction with any system or apparatus in which it may be useful to have buttons, knobs, or other selectors selectively deployed and retracted in response to user selection and/or power availability.

As illustrated, a deployment assembly 760 may be mated with a flow selector assembly 770. The flow selector assembly may include one or more (illustrated as three) manual flow selectors 710, 720, and 730. A knob guard 740 may prevent the manual flow selectors 710, 720, and 730 from being actuated when in a retracted state. The deployment assembly 760 may be configured to selectively deploy the flow selector assembly 770 by translating the flow selector assembly 770 from a retracted position to a deployed position. A manual mode selector 750 may be used to manually select a deployed position. Additionally, the deployment assembly 760 may be configured to deploy the flow selector assembly 770 in response to a power disruption.

Figure 8:
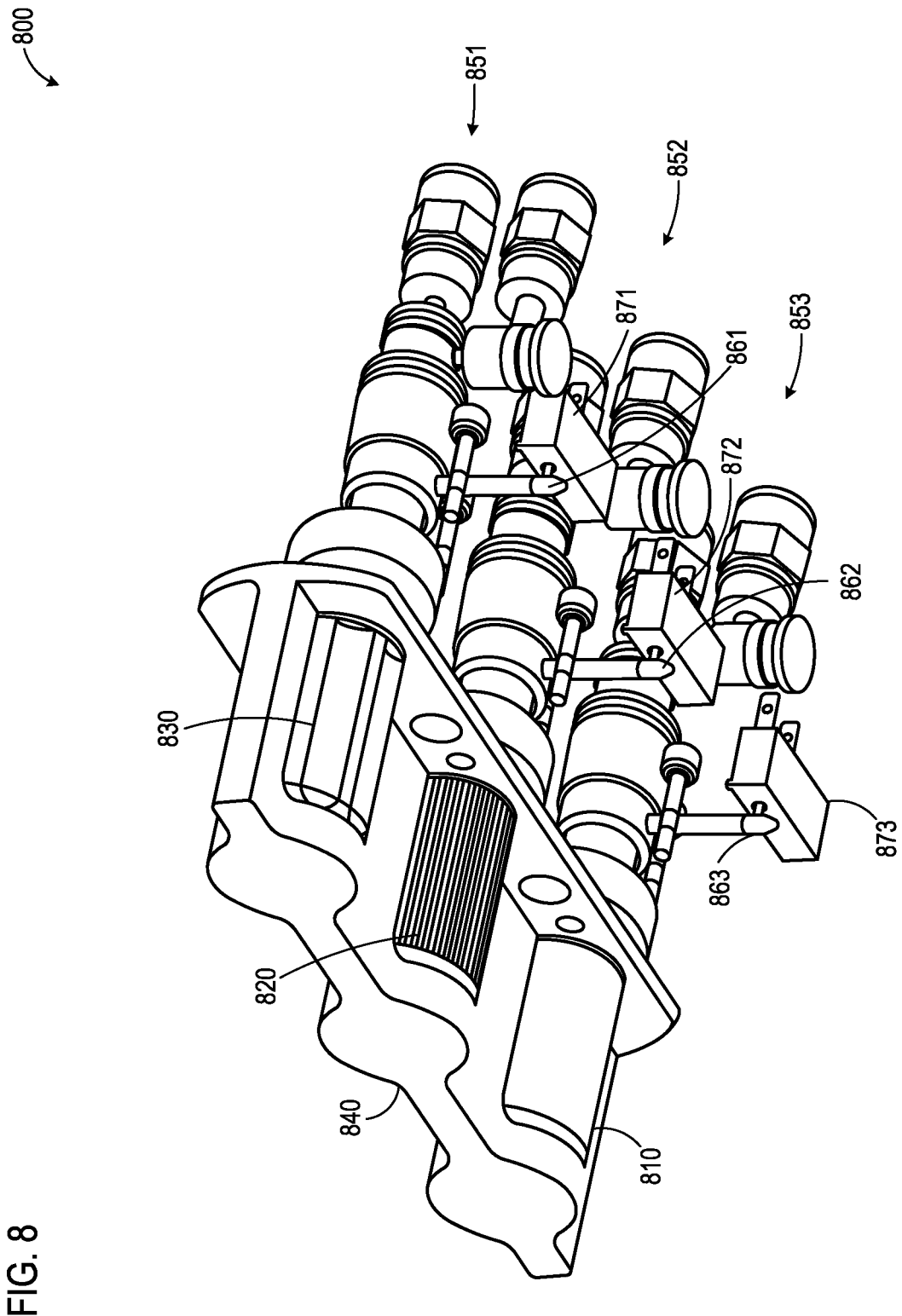
FIG. 8 illustrates a bottom view of three manual flow selectors and associated needle valve assemblies, including position detection components, for controlling the flow rate of three gases.

FIG. 8 illustrates a bottom view 800 of three manual flow selectors 810, 820, and 830 and associated needle valve assemblies 851, 852, and 853 for controlling the flow rate of three gases. Again, a knob guard 840 may prevent each of the manual flow selectors 810, 820, and 830 from being actuated when in a retracted state, prevent axial motion of the manual flow selectors 810, 820, and 830 relative to the front panel, and/or protect the manual flow selectors 810, 820, and 830. The knob guard 840 may be configured to eliminate or reduce potential pinch points during the retraction and/or deployment of the manual flow selectors 810, 820, and 830.

According to various embodiments, each manual flow selector 810, 820, and 830 may have a non-circular cavity that engages a corresponding non-circular valve shaft of each respective needle valve 851, 852, and 853 shaft configured to allow the needle valves 851, 852, and 853 to move axially, independent of the manual flow selectors 810, 820, and 830. Accordingly, the flow rate may be adjusted through axial displacement of each needle valve 851, 852, and 853, yet remain rotationally connected to each respective flow selector 810, 820, and 830 in order to transmit the manual application of torque from a user.

As illustrated, each needle valve 851, 852, and 853 may include a respective valve stop plunger 861, 862, and 863 and position switch 871, 872, and 873, which may function to detect when each respective needle valve 851, 852, and 853 is fully closed or in a home state, as described herein. For example, a valve stop plunger 861, 862, and 863 may be configured to axially travel in conjunction with a valve shaft of each needle valve 851, 852, and 853. When the valve shaft associated with a needle valve 851, 852, and 853 is positioned such that the needle valve 851, 852, and 853 is fully closed or in a home state, the valve stop plunger 861, 862, and 863 may electronically, mechanically, and/or pneumatically indicate the relative position of the associated valve shaft. The position switch 871, 872, and 873 may interface with the valve stop plunger 861, 862, and 863 to detect when the valve shaft is in a predetermined position(s).

Figure 9:
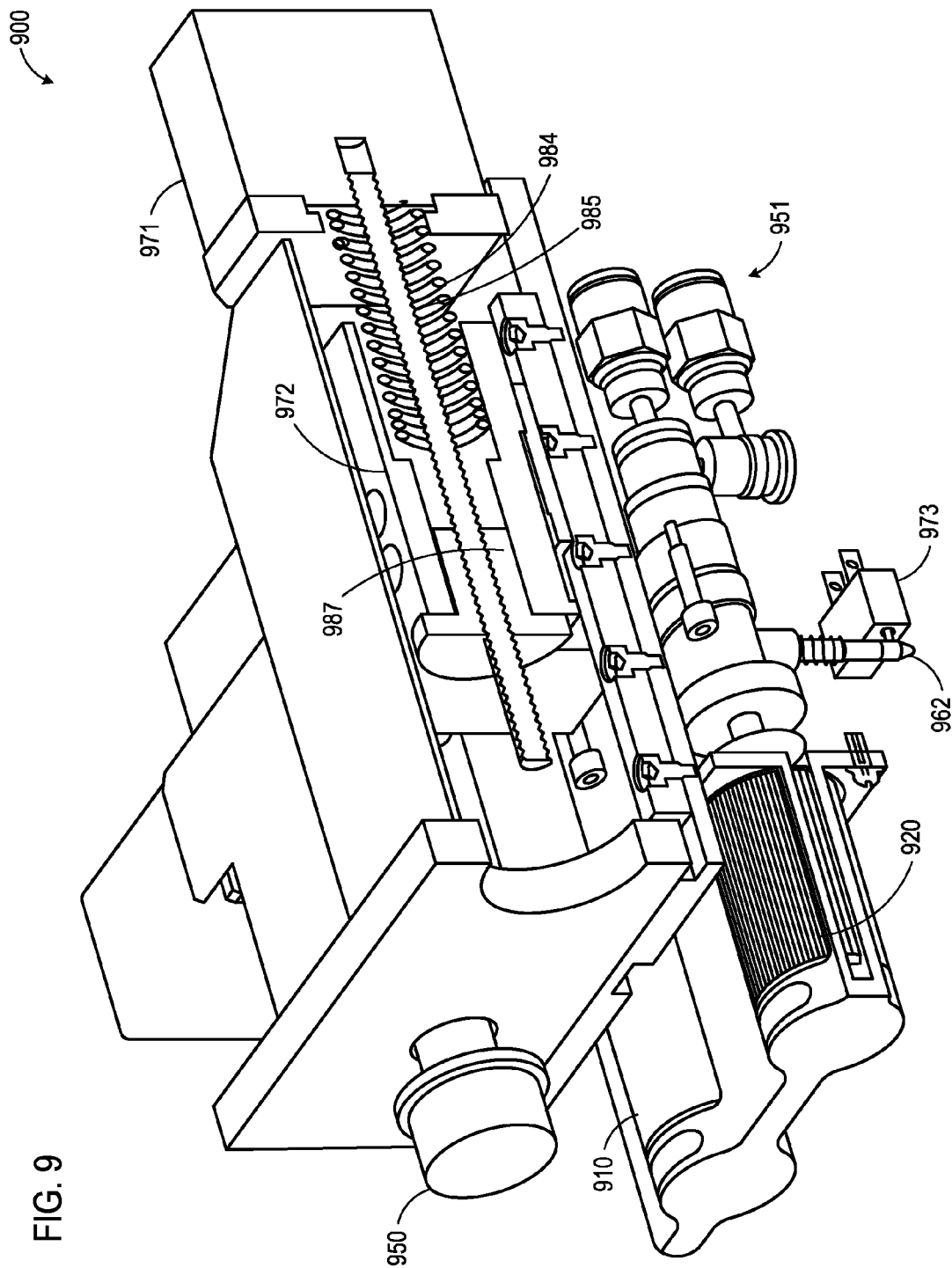
FIG. 9 illustrates a cut-away view of various components within a deployment assembly configured to selectively deploy manual flow selectors within a flow selector assembly.

FIG. 9 illustrates a cut-away view 900 of a portion of the deployment assembly and the flow control assembly. As illustrated, a motor 971 may apply a torque to a threaded shaft 985 to apply a translating force, via a threaded bushing 987, to a junction block 972. The force may be sufficient to overcome the deploying force of a deployment spring 984. The button 950 and associated plunger may be effectively reset for subsequent actuation. Manual flow selectors 910 and 920 may be retracted in conjunction with the retraction of the junction block 972.

FIG. 9 also shows the a top perspective view of a valve stop plunger 962 interfacing with a position switch 973 configured to detect when the valve shaft of a needle valve 951 is positioned such that a predetermined flow rate is achieved. For example, the position switch 973 may be configured to detect when the valve shaft is positioned such that the flow rate of a fluid through the needle valve is zero. Alternatively, the position switch 973 may be configured to detect when the valve shaft is positioned in a home state (as described herein) or fully opened.

Figure 10A:
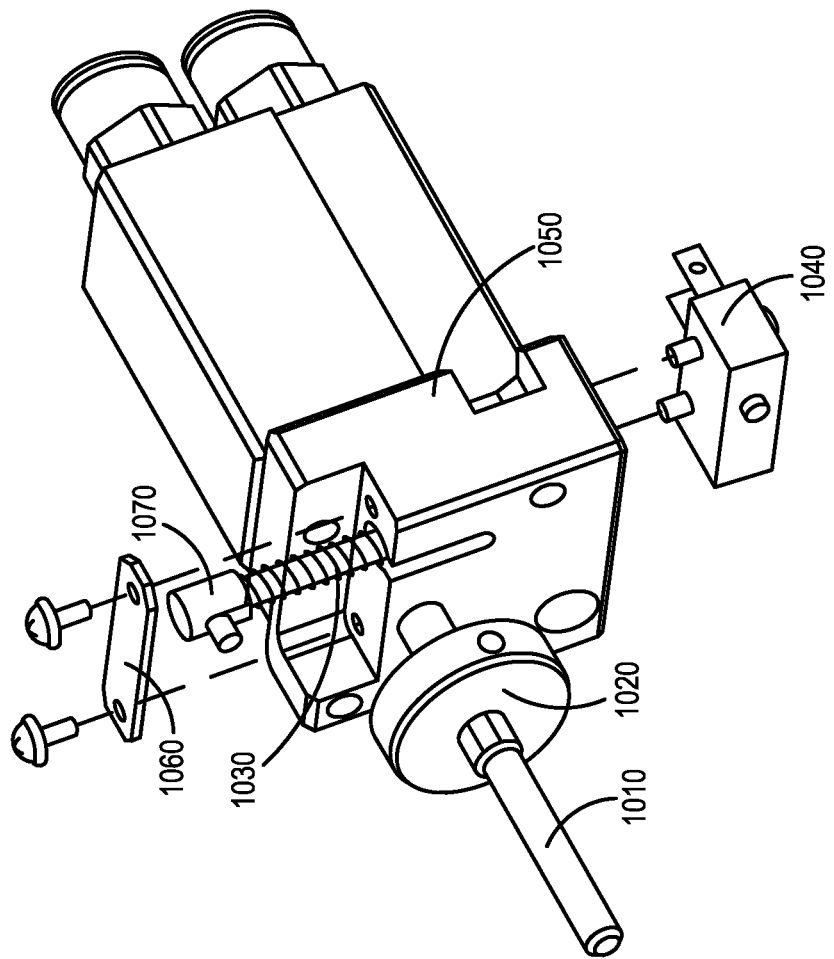
FIG. 10A illustrates an exploded view of a cam assembly configured to actuate a valve stop plunger to interface with a position switch.

FIG. 10A illustrates an exploded view of a cam assembly configured to actuate a valve stop plunger 1070 to interface with a position switch 1040. In the illustrated embodiment, as a valve shaft 1010 is rotated, a cam 1020 may rotate and actuate a valve stop plunger 1070. In the exploded view, a plate 1060 may be used to fasten the spring-actuated valve stop plunger 1070 to a mounting block 1050. A position switch 1040 may also be fastened to the mounting block 1050.

Figure 10B:
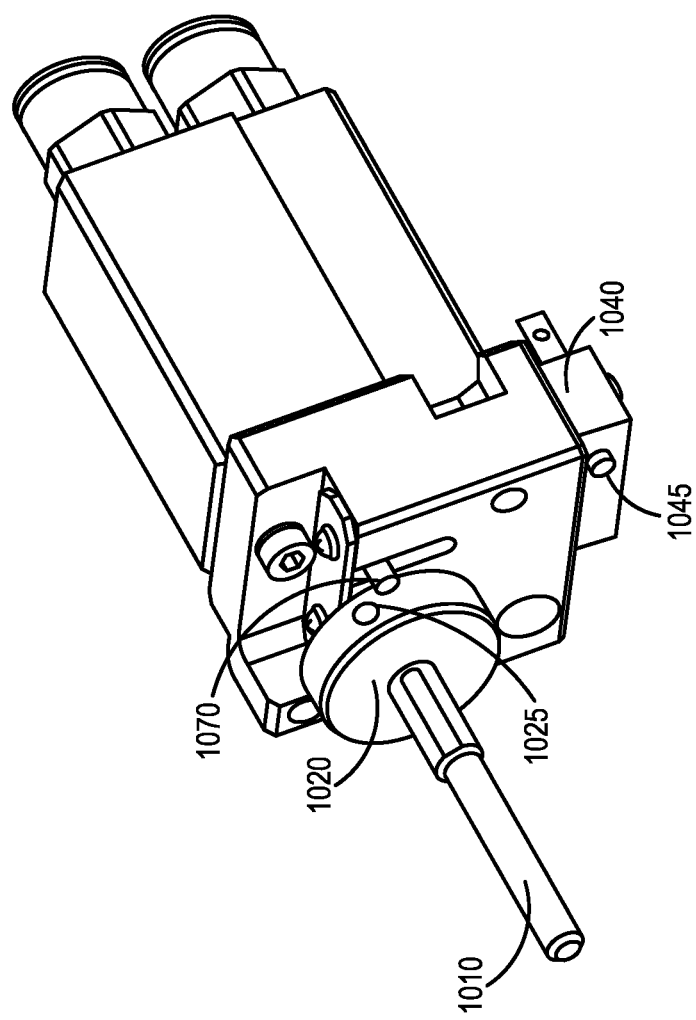
FIG. 10B illustrates an assembled view of a cam assembly configured to actuate a valve stop plunger when a valve shaft is axially translated.

FIG. 10B illustrates an assembled view of a cam assembly configured to actuate a valve stop plunger 1070 when a valve shaft 1010 is axially translated. The axial translation of the valve shaft 1010 is accomplished through rotation of the valve shaft 1010. As the valve shaft 1010 is rotated, an engaging feature 1025 on the cam 1020 may push the valve stop plunger 1070 downward. A tapered end of the valve stop plunger (shown in FIG. 10C) may indicate the axial position of the valve shaft 1010 by interfacing with a sensor 1045 on the position switch 1040. The position switch 1040 may detect the relative location of the valve shaft 1010 when the sensor 1045 is actuated.

Figure 10C:
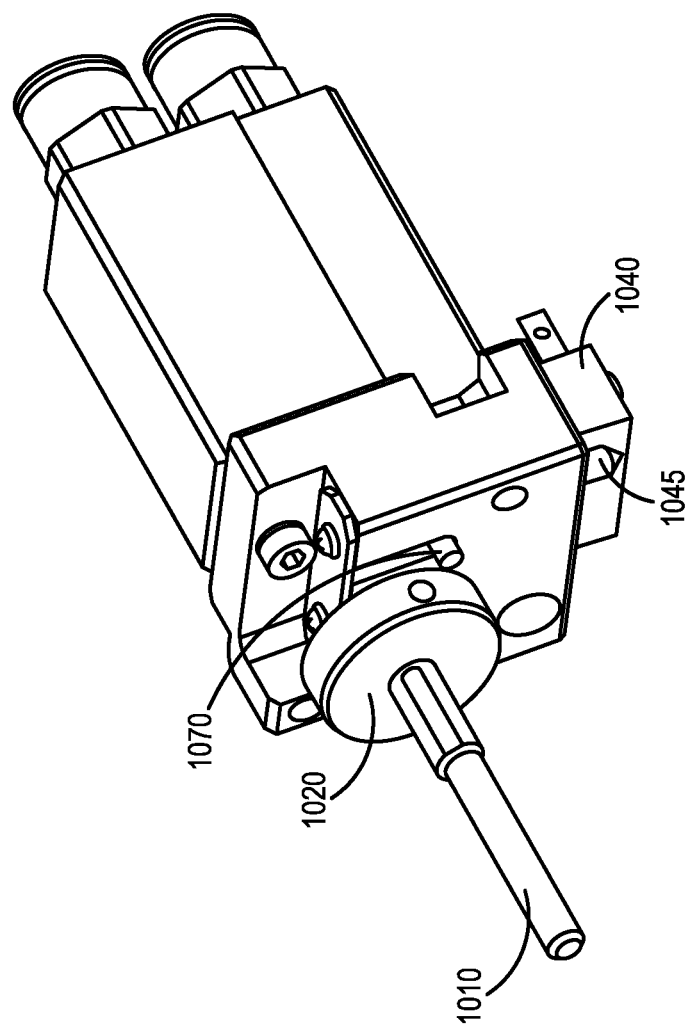
FIG. 10C illustrates a valve stop plunger indicating the position of the valve shaft by interacting with a protrusion on the position switch.

FIG. 10C illustrates the tapered end 1075 of the valve stop plunger 1070 indicating to the position switch 1040 that the valve shaft 1010 has been axially translated (via a rotation). The cam 1020 forced the spring-loaded valve stop plunger downward. As the valve shaft is rotated and axially translated in the opposite direction, the valve stop plunger may rise and no longer engage the sensor (1045 in FIG. 10B) of the position switch 1040.

FIG. 11A illustrates an exploded view of a flow selector assembly and associated needle valves 1160, 1161, and 1162. As illustrated, a knob guard 1140 may be configured to surround, protect, and prevent axial movement of flow selectors (knobs) 1110, 1120, and 1130. A mounting surface 1150 may be configured to allow valve shafts of each of the needle valves 1160, 1161, and 1162 to axially translate while preventing the flow selectors 1110, 1120, and 1130 from axially translating.

Figure 11B:
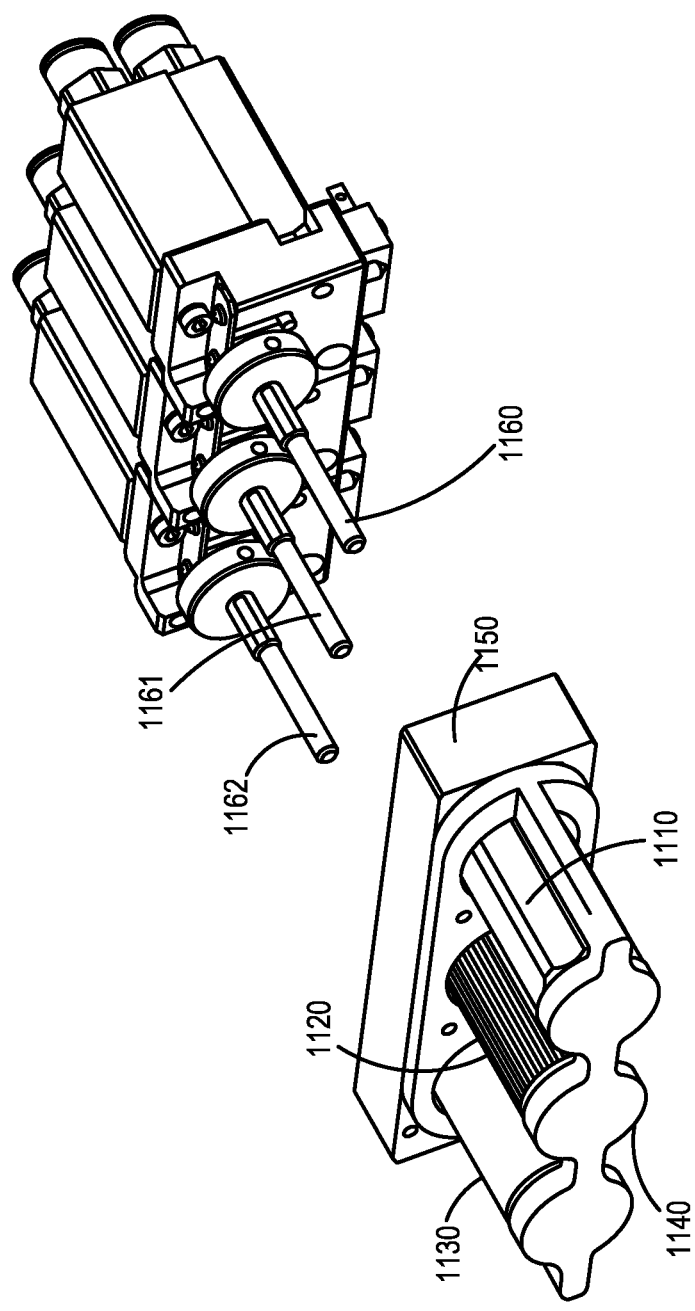
FIG. 11B illustrates another exploded view of the flow selector assembly and associated needle valves.

FIG. 11B illustrates the flow selectors 1110, 1120, and 1130 assembled with the knob guard 1140 and mounting surface 1150. The valve shafts of the needle valves 1160, 1161, and 1162 may be configured to rotationally engage the flow selectors 1110, 1120, and 1130. Rotating the flow selectors 1110, 1120, and 1130 may increase or decrease the flow rate of a fluid by axially translating the valve shafts.

Figure 11C:
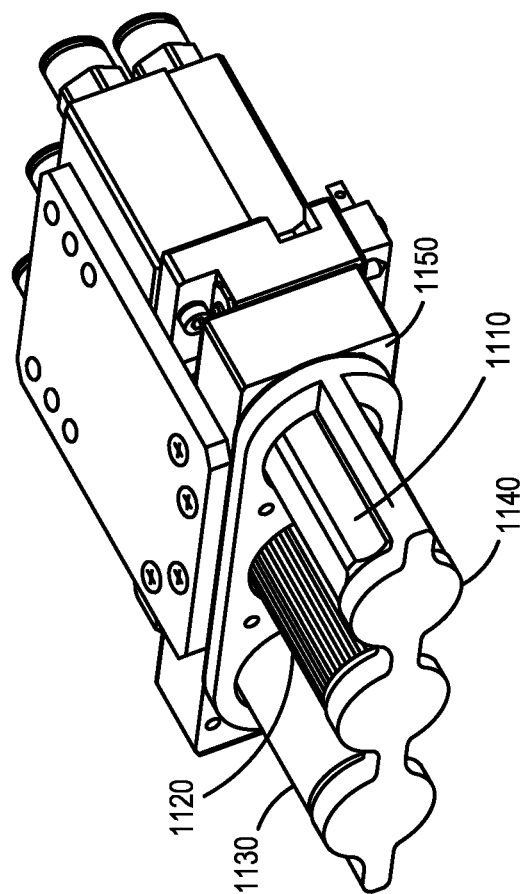
FIG. 11C illustrates an assembled view of the flow selector assembly.

FIG. 11C illustrates an assembled view of the flow selector assembly, including the knob guard 1140, the flow selectors 1110, 1120, and 1130, and the mounting surface 1150.

Figure 12A:
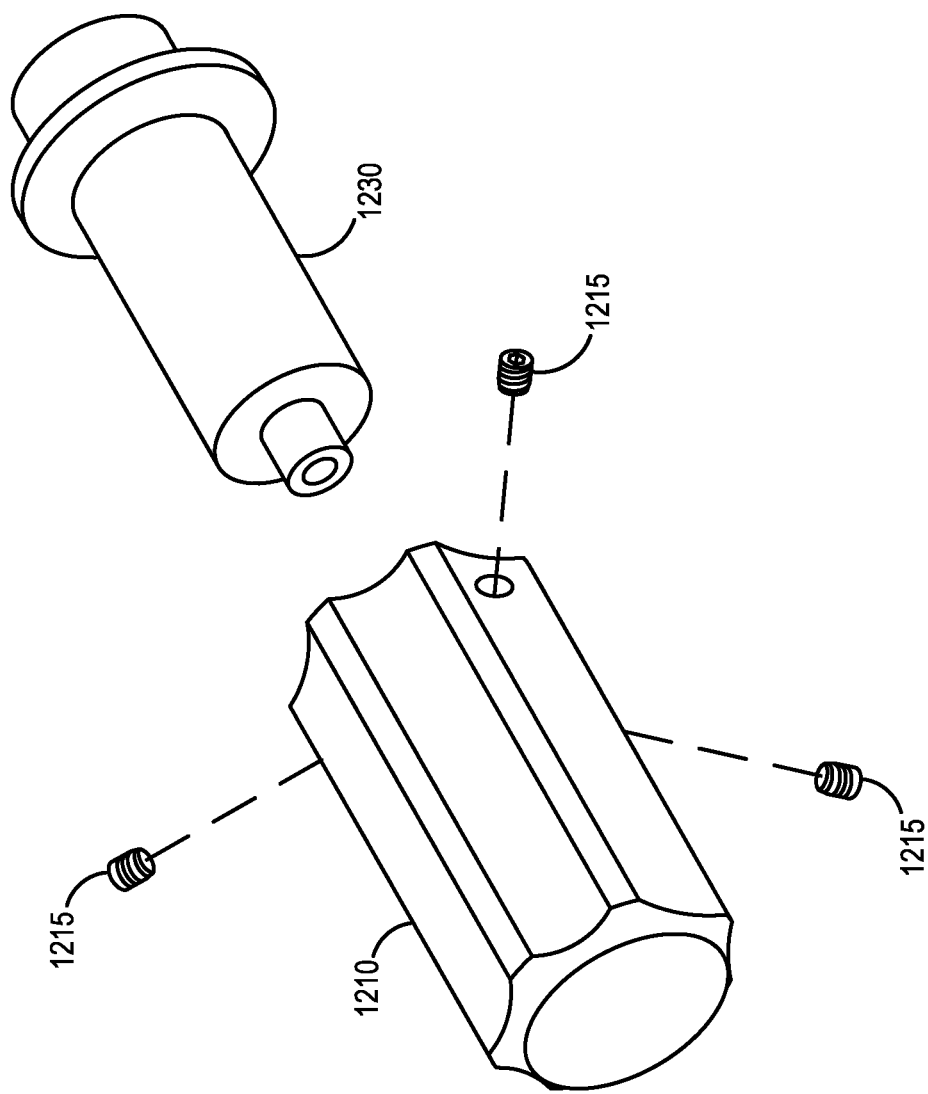
FIG. 12A illustrates a flow selector configured to be mated with an engagement cylinder view set screws.

FIG. 12A illustrates a flow selector 1210 configured to be mated with an engagement cylinder 1230 via set screws 1215. As illustrated, the flow selector 1210 may be rotationally engaged with the engagement cylinder 1230 by tightening the set screws 1215. In some embodiments, the engagement cylinder 1230 may include flat surfaces, slots, and/or holes configured to receive the set screws 1215.

Figure 12B:
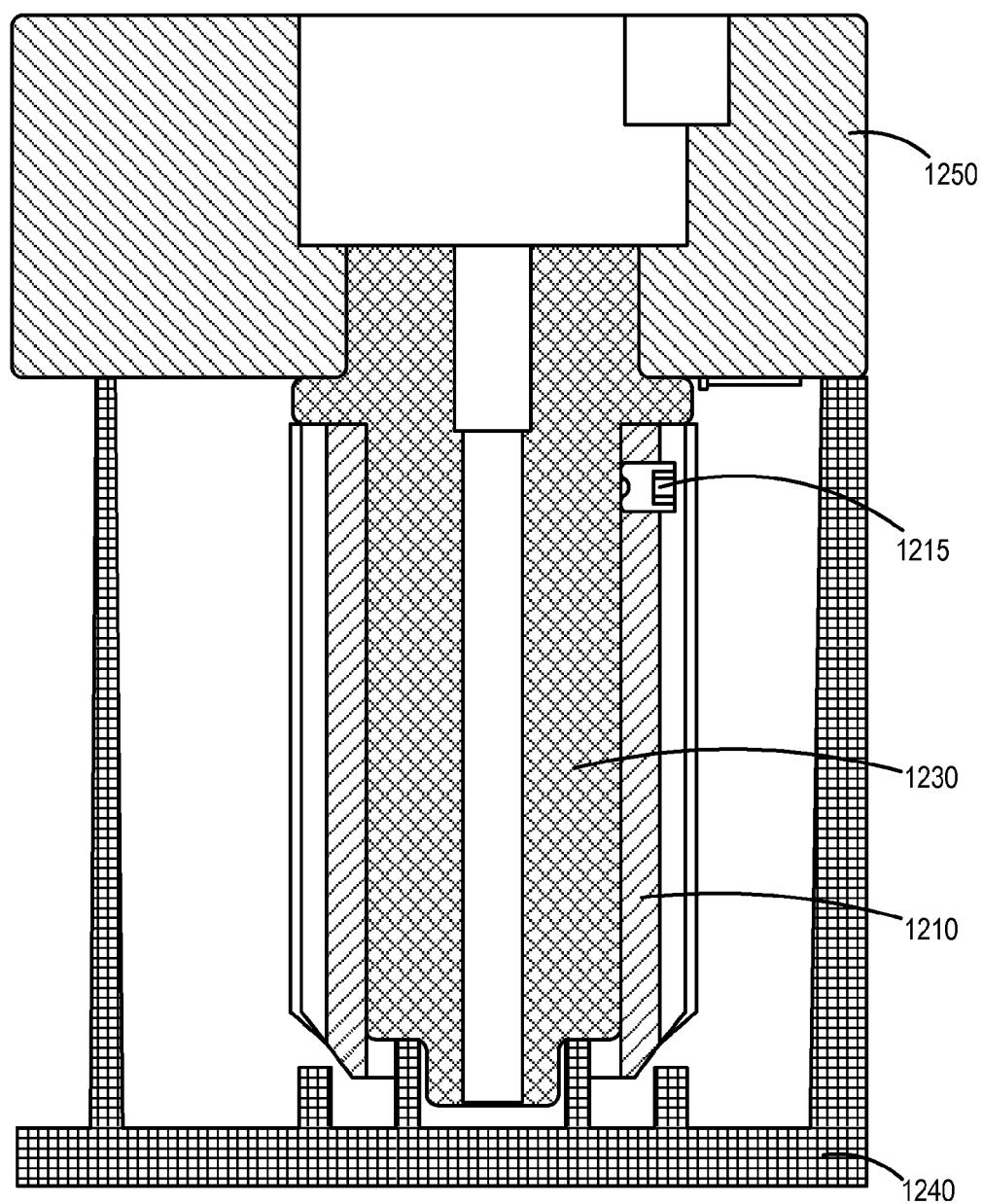
FIG. 12B illustrates a cross sectional view of the flow selector, engagement cylinder, and set screws.

FIG. 12B illustrates a cross sectional view of the flow selector 1210, engagement cylinder 1230, and a set screw 1215. In some embodiments, the flow selector 1210 and cylinder 1230 may be configured to remain rotationally engaged (due to the force of the set screw 1215), but free to axially translate with respect to one another. In other embodiments, the flow selector 1210 and cylinder 1230 may be configured to remain rotationally engaged (due to the force of the set screw 1215) and axially fixed with respect to one another.

Figure 13:
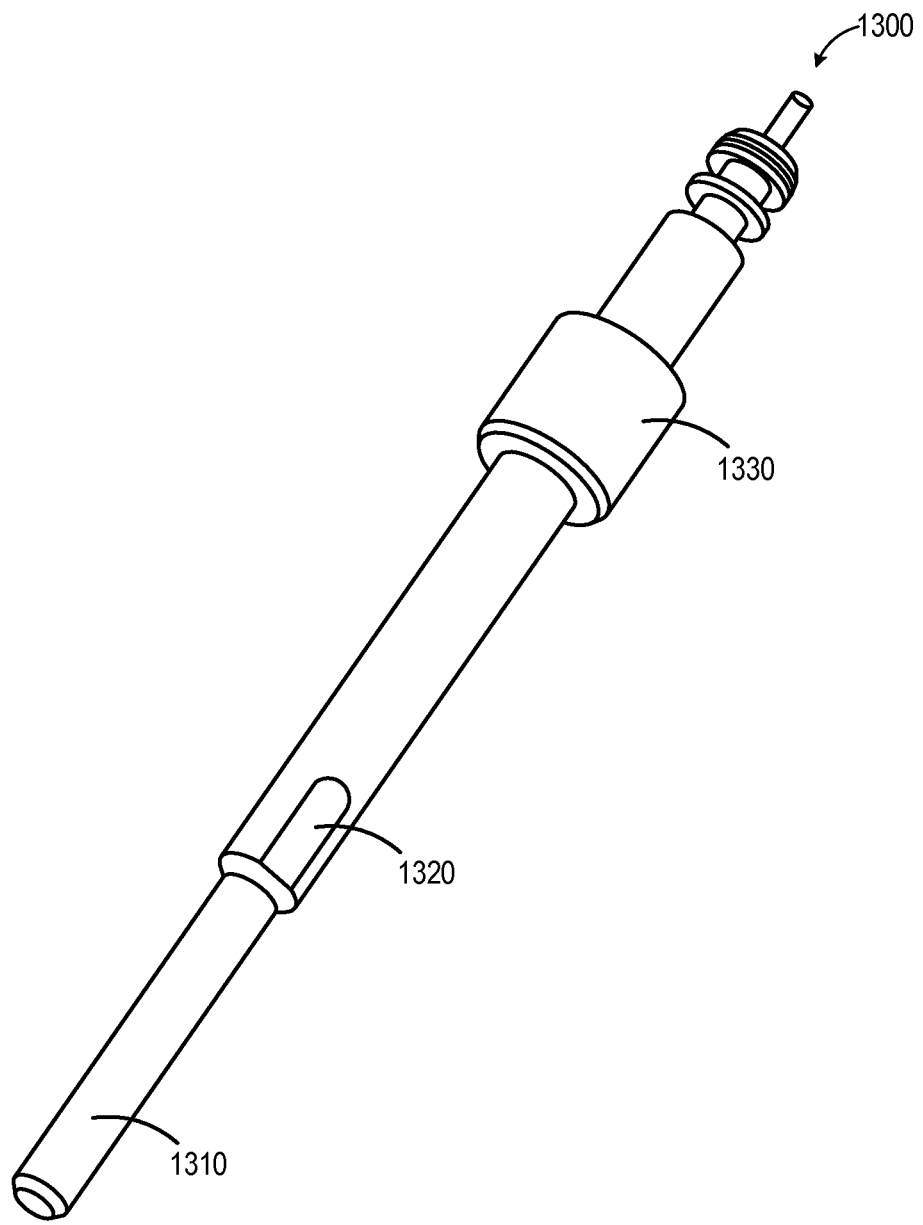
FIG. 13 illustrates a valve shaft including an engagement surface configured to allow the valve shaft to axially translate while remaining rotationally engaged with a flow selector.

FIG. 13 illustrates a valve shaft 1300 including an engagement surface 1320 configured to allow the valve shaft 1300 to axially translate while remaining rotationally engaged with a flow selector. The valve shaft may include an end 1310 for engaging a flow selector and an end 1330 for controlling the flow rate of a fluid.

Figure 14:
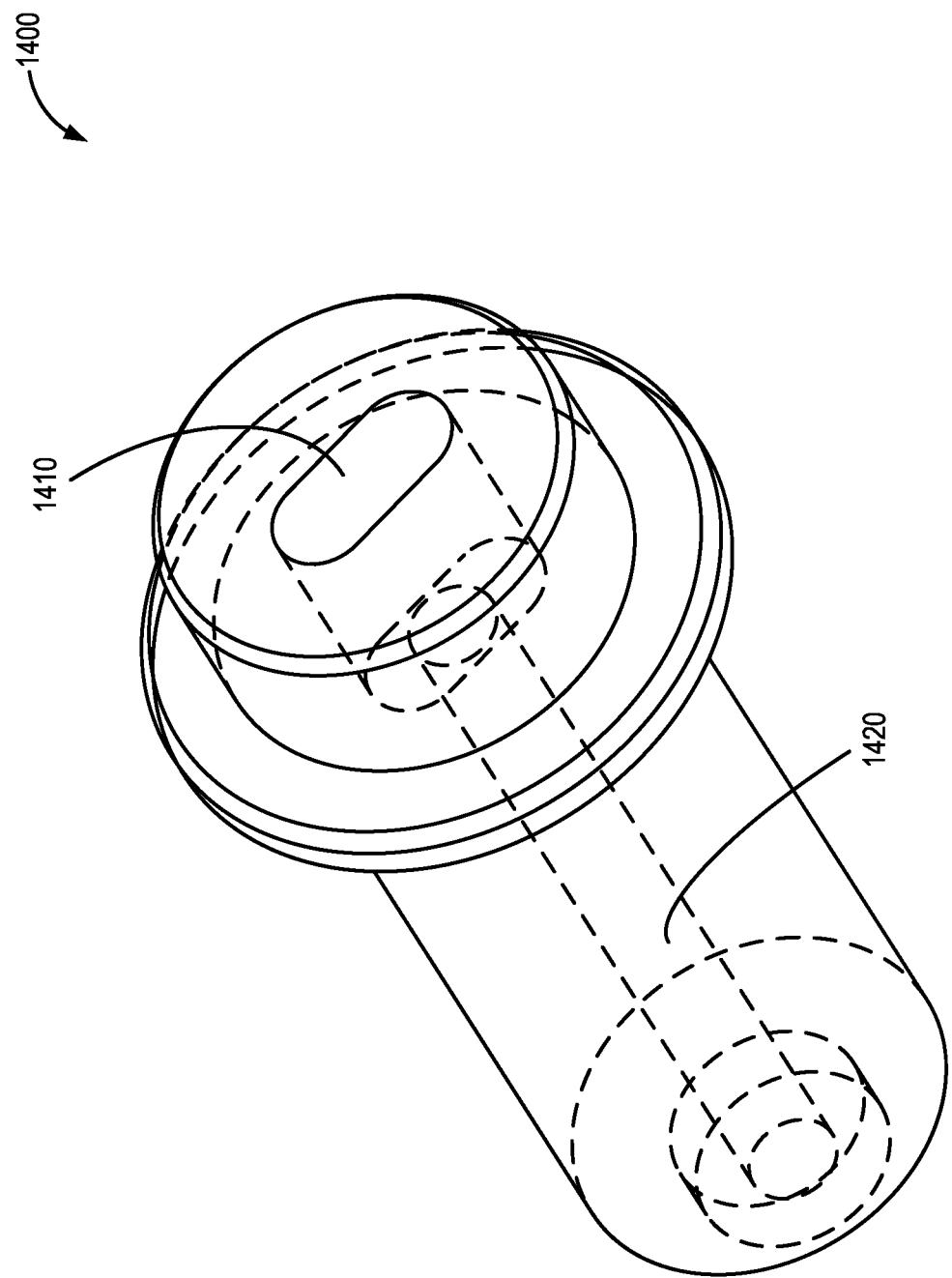
FIG. 14 illustrates an engagement cylinder configured to rotationally engage a valve shaft and remain axially free to translate with respect to a flow selector.

FIG. 14 illustrates an engagement cylinder 1400 configured to rotationally engage a valve shaft and remain axially free to translate with respect to a flow selector. The engagement cylinder 1400 may include a circular aperture 1420 and a non-circular (e.g., polygonal, elliptical, and/or circular with a protrusion or key formation) engagement feature configured to allow the engagement cylinder to rotationally engage a valve shaft.

Figure 15A:
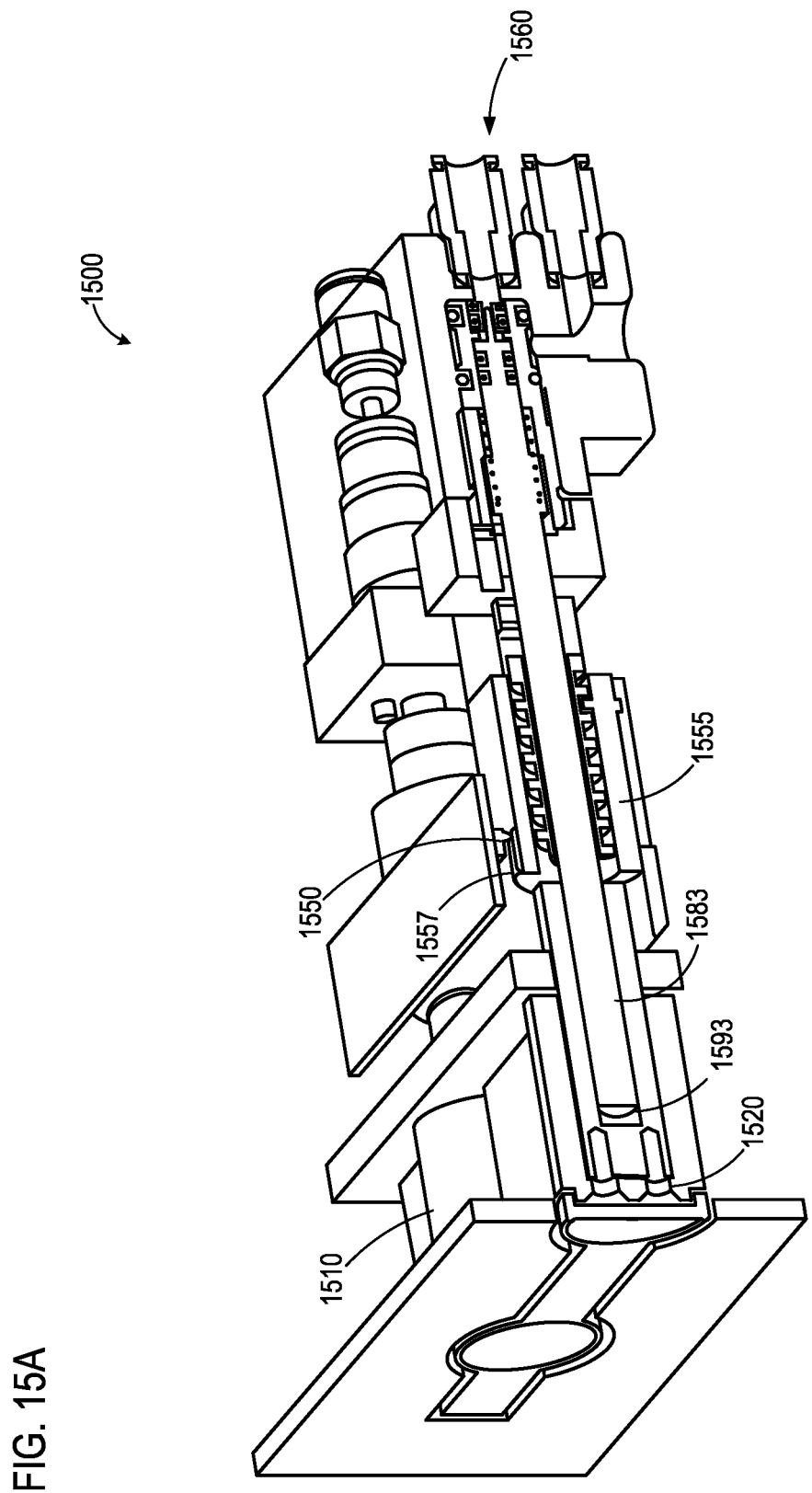
FIG. 15A illustrates a cut-away view of a deployment assembly with a flow selector assembly in a retracted state and a needle valve in a fully closed state.

FIG. 15A illustrates a cross-sectional view of a flow selector assembly 1500 in which a position detector 1550 confirms that a valve shaft 1583 of a needle valve 1560 is in a home state. As illustrated, the position detector 1550 may comprise a detect switch configured to engage a protruding or raised portion 1557 of an axially-floating bushing 1555. The axially-floating bushing 1555 may be configured to translate axially with the valve shaft 1583, but not rotate as the valve shaft 1583 is rotated. In other embodiments, a bushing may be configured to rotate and translate together with the valve shaft 1583. The position detector 1550 may be actuated only when the detect switch engages the protruding portion 1557 of the axially-floating bushing.

The valve shaft 1583 may be configured to engage a cavity 1593 in a flow selector 1520. As previously described, the valve shaft 1583 may be free to translate axially within the cavity 1593, while remaining rotationally engaged. The cavity and/or the valve shaft may be any non-circular shape, such as square, hexagonal, or circular with protrusions/intrusions.

The position detector 1550 and position indicator (the raised portion 1557 of the axially floating bushing 1555) may be configured such that the position detector 1550 detects when the valve shaft 1583 is fully opened, fully closed, and/or at a home state. The home state may correspond to a predetermined or threshold flow rate. According to various embodiments, the mechanical needle valve 1560 may be adjustable between a fully closed state, in which no gas flows, a fully open state, in which a maximum amount of gas flows, and any flow rate therebetween. In some embodiments, the needle valve 1560 may be configured to enter a home state when the flow selector 1520 is retracted.

FIG. 15A illustrates flow selectors 1510 and 1520 in a retracted state with the needle valve 1560 in a fully closed position (i.e., the flow rate is zero). In the fully closed position, the protrusion 1557 on the axially-floating bushing 1555 associated with the valve shaft 1583 allows the position detector 1550 to detect that the needle valve 1560 is in a fully closed position.

Figure 15B:
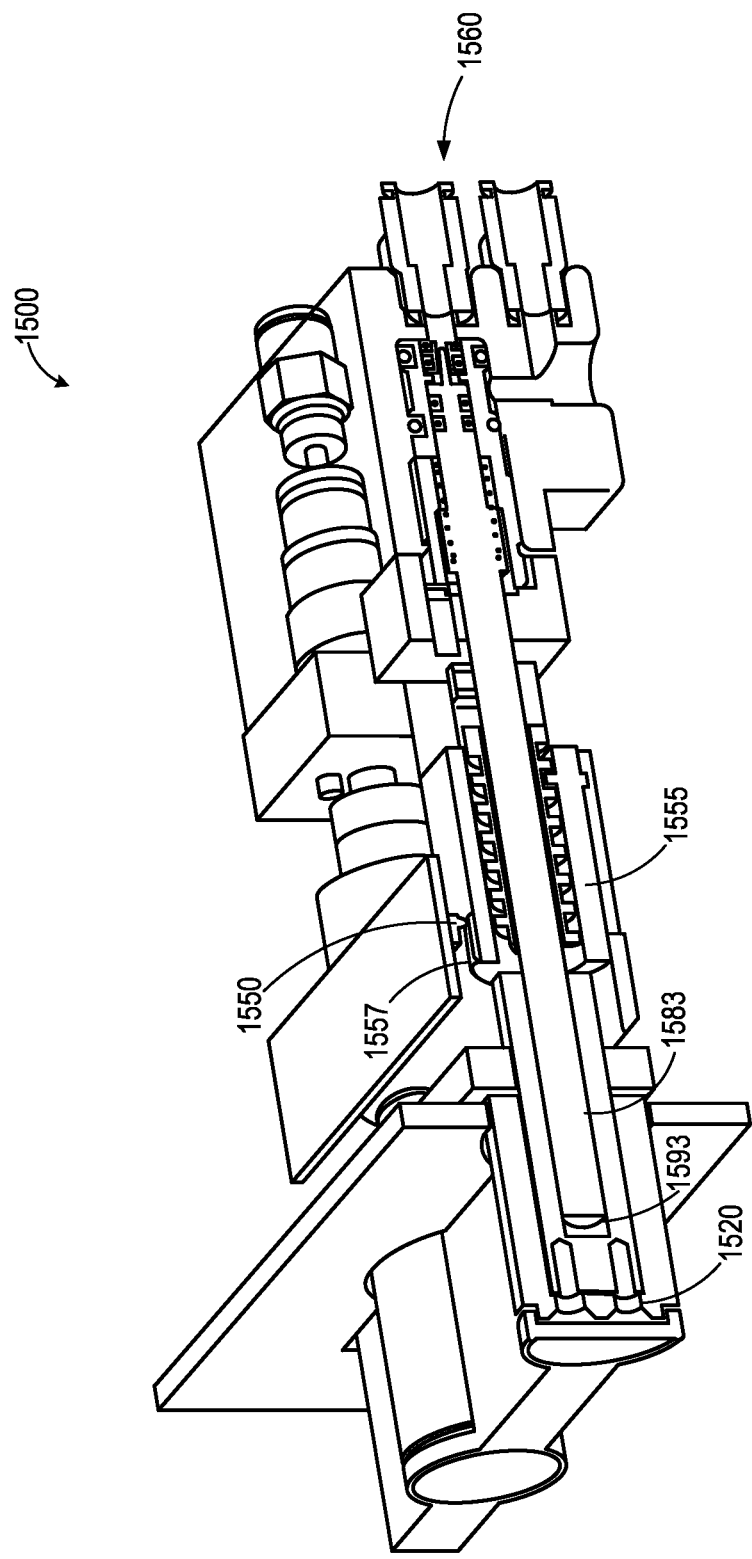
FIG. 15B illustrates a cut-away view of a deployment assembly with a flow selector assembly in a deployed state and a needle valve in the fully closed state.

FIG. 15B illustrates the flow selector 1520 in a deployed state. The needle valve 1560 is still fully closed with the protrusion 1557 engaging the position detector 1550. Accordingly, the position detector 1550 may detect that the needle valve 1560 is in a fully closed position with a flow rate of zero. As previously described, in an alternative embodiment, the protrusion 1557 and/or position detector 1550 may be configured such that the position detector 1550 may detect when the needle valve 1560 is fully opened, is at a particular flow rate, and/or is within a particular flow rate range.

In some embodiments, an axially-floating bushing may include multiple protrusions and/or inclusions and varying heights and/or depths. A position detector may be capable of detecting one or more flow rates and/or valve shaft positions.

Figure 15C:
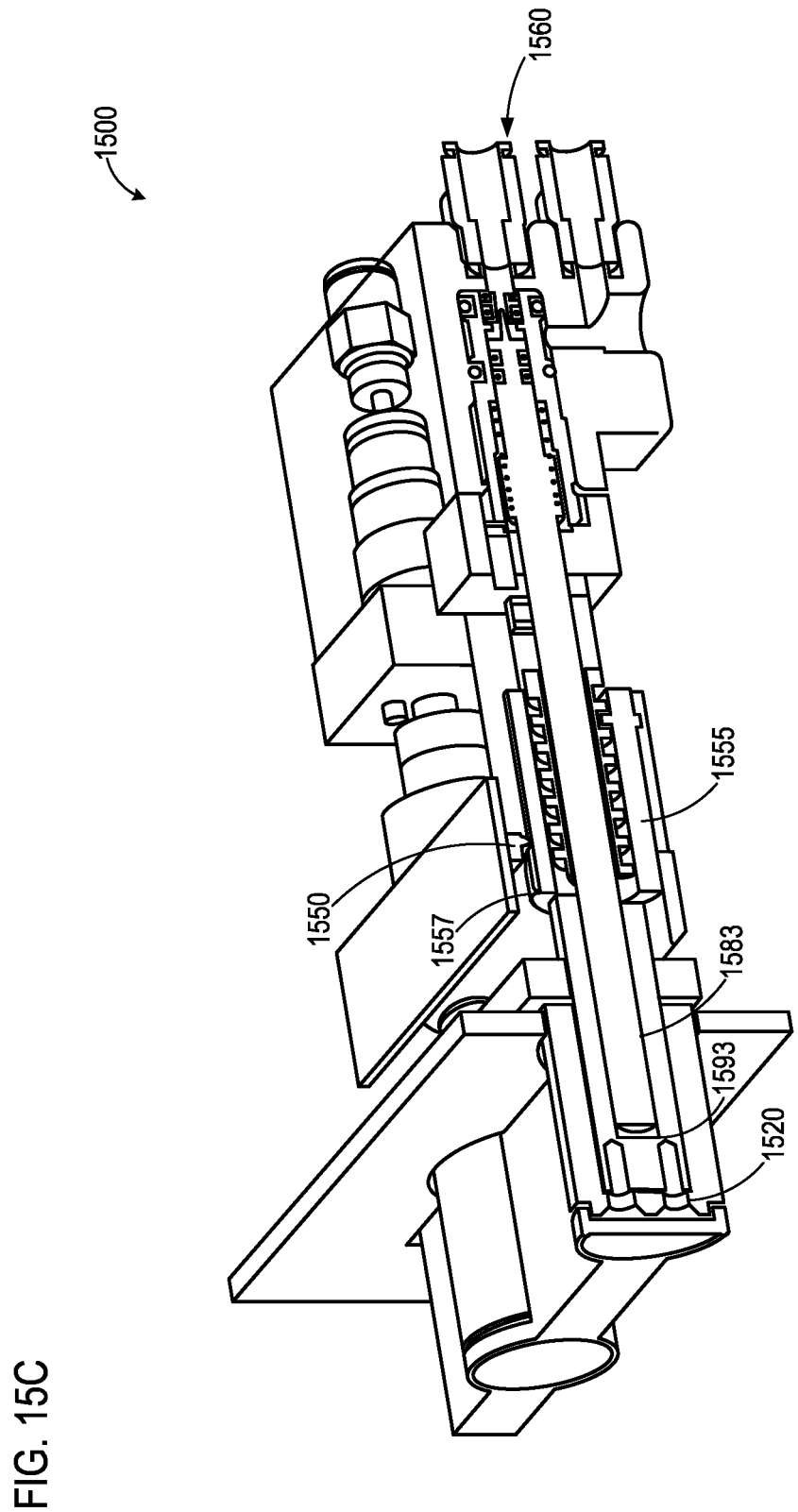
FIG. 15C illustrates a cut-away view of a deployment assembly with a flow selector assembly in a deployed state and a needle valve in a partially opened state.

FIG. 15C illustrates the flow selector 1520 in a deployed state with the valve shaft 1583 partially opened relative to the other components of the needle valve 1560. As illustrated, the position detector 1550 may no longer engage the protrusion 1557. Accordingly, the position detector 1550 may detect that the needle valve is not in a fully closed state with a flow rate of zero.

Figure 15D:
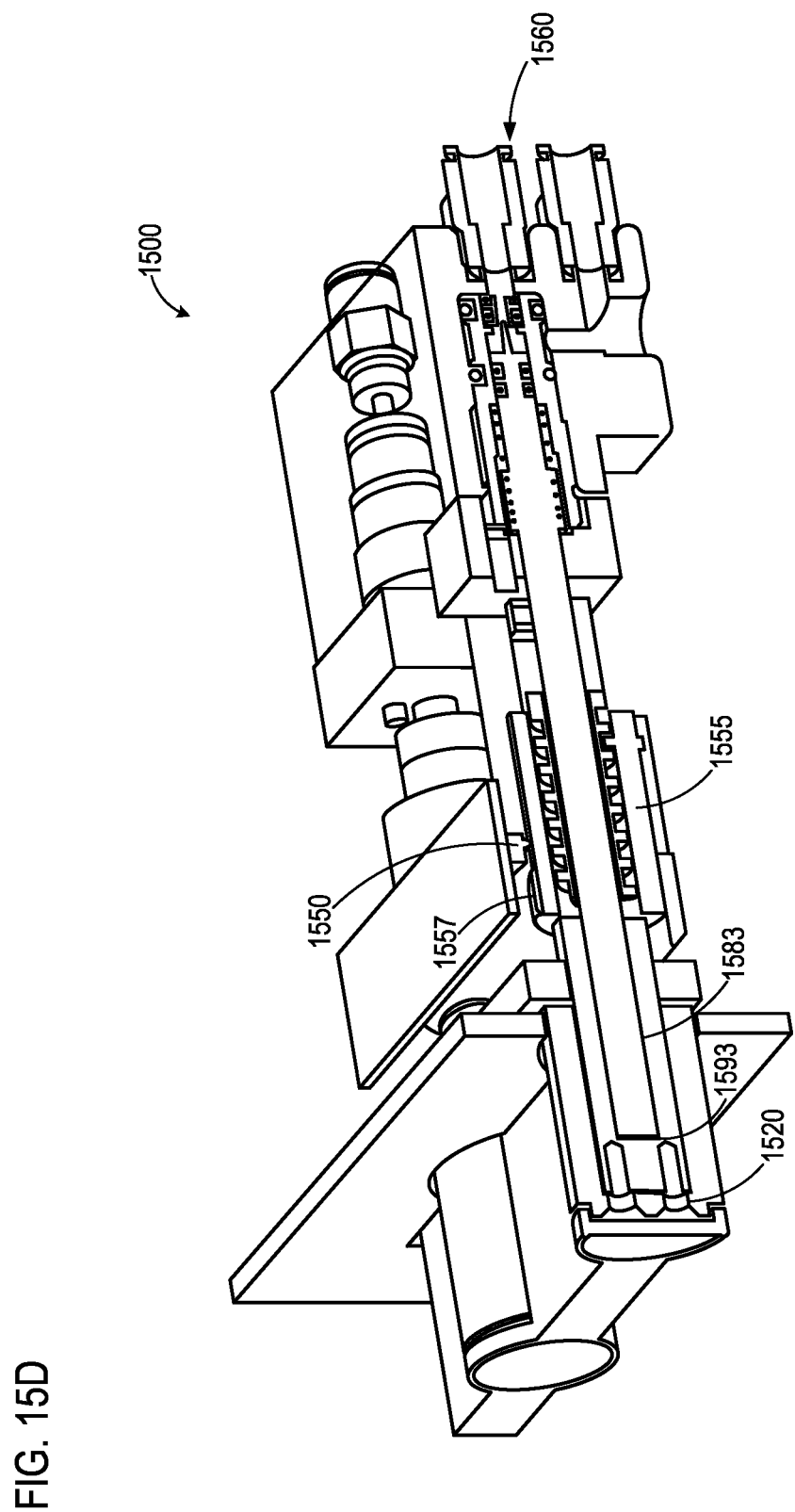
FIG. 15D illustrates a cut-away view of a deployment assembly with a flow selector assembly in a deployed state and a needle valve in a fully opened state.

FIG. 15D illustrates the flow selector 1520 in a deployed state with the valve shaft 1583 fully translated toward the flow selector 1520. As illustrated, the position detector 1550 may not engage the protrusion 1557 on the axially-floating bushing 1555.

As previously described, one or more of the needle valves in a flow control valve assembly may be configured to return to a home state when the flow selectors are retracted rather than in a fully closed state. In such embodiments, a three-way selector valve (or other diversion valve system) may prevent any gas from actually flowing when the flow selector is retracted. When the flow selector is deployed, it will automatically allow an amount of gas corresponding to the home state of the needle valve to flow. For example, the home state may correspond to a flow rate of oxygen of 2 liters per minute and a flow rate of nitrous oxide and/or air of 0 liters per minute. Various possible home state flow rates are possible for each available gas.

FIG. 16A illustrates another view of a flow selector assembly 1600 with position detectors (detect switches 1671, 1672, and 1673) configured to selectively detect the relative location of valve shafts 1691, 1692, and 1693. As described in conjunction with FIG. 15A-15D, the position detectors 1671, 1672, and 1673 may be configured to detect whether or not they are engaged with protrusions (such as protrusion 1663) on a groove 1661, 1662, and 1663 on a bushing 1665, 1666, and 1667.

In the illustrated embodiment, needle valves 1651 and 1652 may be fully closed with the valve shafts 1691 and 1692 fully translated toward the needle valves 1651 and 1652. Accordingly, position detectors 1671 and 1672 may engage a protrusion (not illustrated) and detect that the needle valves 1651 and 1652 are fully closed. Valve shaft 1693 may be fully translated toward the flow selector 1630, causing needle valve 1653 to be fully opened. Position detector 1673 may not be engaged with protrusion 1663, and therefore detect that the needle valve 1653 is not fully closed.

FIG. 16A also shows three possible embodiments of valve shaft shapes. A first valve shaft 1693 may be hexagonal in shape and configured to engage a hexagonal cavity 1683 of a flow selector 1630. A second valve shaft 1692 may be rectangular in shape and configured to engage a rectangular cavity 1682 of a flow selector 1620. A third valve shaft 1691 may be circular in shape and include two protrusions configured to engage corresponding inclusions in a round cavity of a flow selector 1610. According to various embodiments, the cavities 1681, 1682, and 1683 may rotationally engage the valve shafts 1691, 1692, and 1693, but leave the valve shafts 1691, 1692, and 1693 free to axially translate relative to the flow selectors 1610, 1620, and 1630. In various embodiments, a knob guard 1640 may prevent axial translation of the flow selectors 1610, 1620, and 1630.

Figure 16B:
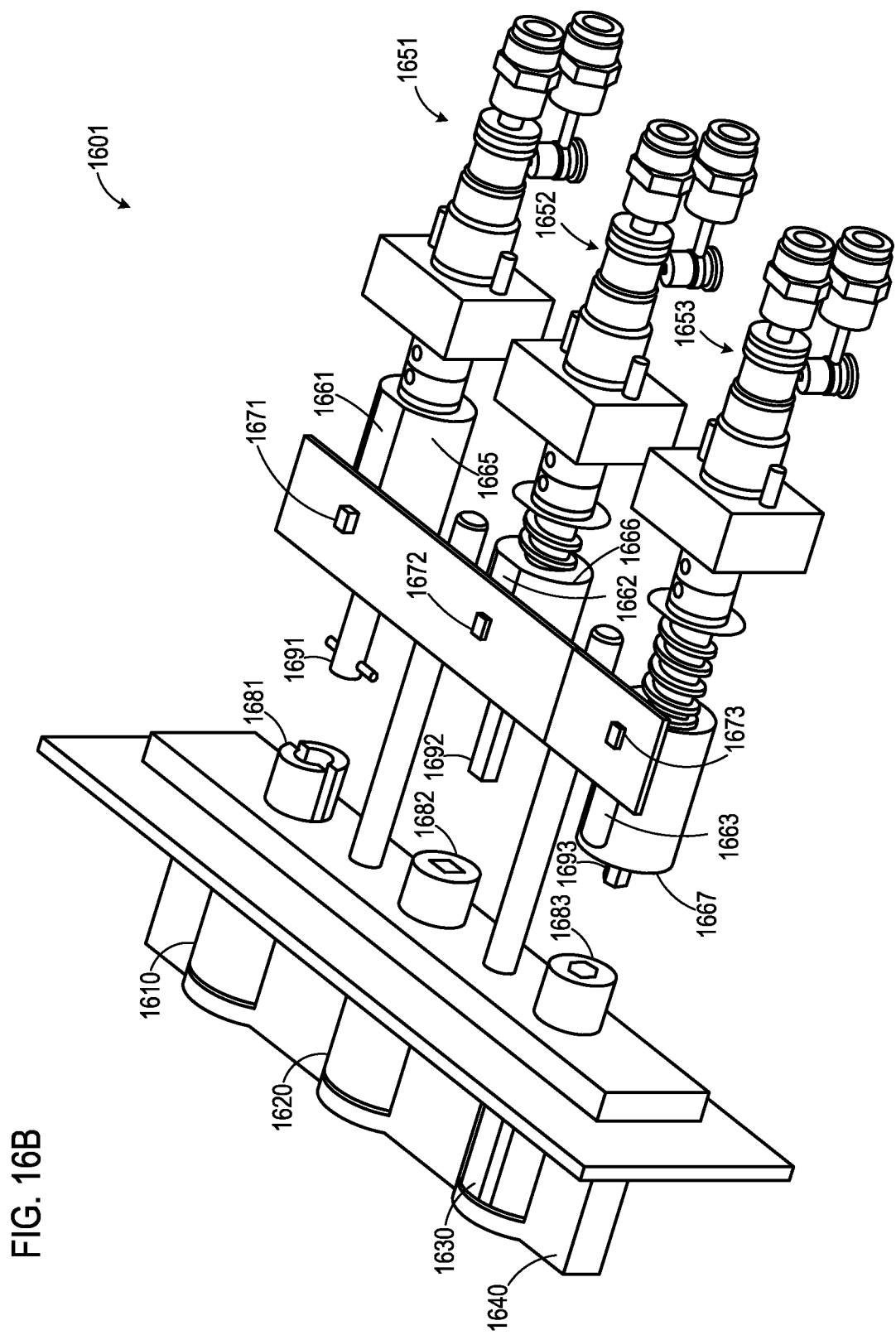
FIG. 16B illustrates a top exploded view of a flow selector assembly showing the possible embodiments of engagement cavities formed in the flow selectors and corresponding valve shafts.

FIG. 16B illustrates a top exploded view of a flow selector assembly 1601 showing three possible embodiments of engagement cavities 1681, 1682, and 1683 formed in the flow selectors 1610, 1620, and 1630 and corresponding valve shafts 1691, 1692, and 1693. The engagement cavities and/or valve shafts may be any non-circular shape, such that the valve shaft remains rotationally engaged while still free to axially translate. For example, the engagement cavity and valve shaft may include N number of equal or unequal sides, where N is an integer, non-circular with curved surfaces, circular with protrusions, and/or any other shape that maintains the valve shaft rotationally engaged with the flow selectors and free to axially translate.

A gas flow control system, according to any of the various embodiments described herein, may be used in conjunction with any of a wide variety of applications. In the illustrated embodiments, the gas flow control systems are shown as parts of anesthesia delivery systems. In such embodiments, the combined flow of one or more gases may be injected or otherwise infused with anesthesia, such as via a vaporizer, for a controlled delivery of the anesthesia and/or the one or more gases to a patient.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A valve assembly for controlling the flow rate of a fluid, comprising:
    a valve housing defining a flow channel configured to allow a fluid to flow from an input to an output;
    a valve shaft having a first end and a second end defining an axis, the valve shaft configured such that rotation of the valve shaft causes the valve shaft to axially translate within the flow channel to control a flow rate of the fluid from the input to the output;
    a rotatable flow selector configured to remain in a fixed position axially with respect to the valve housing;
    an engagement cavity in the rotatable flow selector configured to receive the first end of the valve shaft, such that rotation of the rotatable flow selector causes a rotation of the valve shaft;
    a position indicator associated with the axial translation of the valve shaft relative to the flow channel wherein the position indicator comprises a valve stop plunger in an axially fixed position relative to the valve shaft, such that the valve stop plunger remains in a fixed position as the valve shaft is axially translated wherein the valve stop plunger is configured to move tangentially with respect to the rotation of the valve shaft;
a position detector configured to be actuated by the valve stop plunger when the valve shaft is axially translated such that the flow rate of the fluid from the input to the output corresponds to the threshold flow rate; and
a rotating valve stop plunger actuator associated with the valve shaft, the valve stop plunger actuator configured to rotate with the valve shaft and move the valve stop plunger relative to the position detector based on the relative axial location of the valve shaft with respect to the flow channel,
wherein the valve shaft is free to translate axially within the engagement cavity while remaining rotationally engaged with the rotatable flow selector.

2. The valve assembly of claim 1, wherein the engagement cavity is defined by walls forming an n-sided polygonal shape, where n is an integer greater than 2.

3. The valve assembly of claim 1, wherein the engagement cavity is defined by a wall forming a non-circular ellipse.

4. The valve assembly of claim 1, wherein the engagement cavity is defined by one or more walls forming a non-circular shape.

5. The valve assembly of claim 1, wherein the engagement cavity is circular in shape with a key formation configured to interface with a corresponding key formation on the valve shaft, such that rotation of the rotatable flow selector causes a rotation of the valve shaft.

6. The valve assembly of claim 1, wherein the valve assembly is configured for use in an anesthesia delivery system.

7. A valve assembly for controlling the flow rate of a fluid, comprising:
a valve housing defining a flow channel configured to allow a fluid to flow from an input to an output;
a valve shaft having a first end and a second end defining an axis, the valve shaft configured such that rotation of the valve shaft causes the valve shaft to axially translate within the flow channel to control a flow rate of the fluid from the input to the output;
a flow selector in communication with the valve shaft, such that actuation of the flow selector causes a rotation of the valve shaft;
a position indicator associated with the axial translation of the valve shaft relative to the flow channel, wherein the position indicator comprises a valve stop plunger in a fixed position, such that the valve stop plunger remains in the fixed position as the valve shaft is axially translated wherein the valve stop plunger is configured to move tangentially with respect to the rotation of the valve shaft;
a position detector configured to interface with the position indicator to detect when the valve shaft is axially translated such that the flow rate of the fluid from the input to the output corresponds to a threshold flow rate; and
a rotating actuator mechanically coupled to the valve shaft, the actuator configured to rotate with the valve shaft and move the valve stop plunger relative to the position detector based on the relative axial location of the valve shaft with respect to the flow channel.

8. The valve assembly of claim 7, wherein the actuator comprises a protrusion integrally formed on the valve shaft configured to move the valve stop plunger relative to the position detector as the valve shaft is axially translated.

9. The valve assembly of claim 7, wherein the actuator is integrally coupled to the valve shaft.

10. The valve assembly of claim 7, wherein the actuator comprises a cam configured to move the valve stop plunger relative to the position detector based on the relative axial location of the valve shaft with respect to the flow channel.

11. The valve assembly of claim 7, wherein the threshold flow rate corresponds to a minimum safe flow rate of a medically required gas, such that the flow rate of the fluid from the input to the output is the minimum safe flow rate of the medically required gas.

12. The valve assembly of claim 11, wherein the medically required gas comprises oxygen and the minimum safe flow rate is between 1 liter per minute and 2 liters per minute.

13. The valve assembly of claim 7, wherein the threshold flow rate corresponds to zero, such that the flow rate of the fluid from the input to the output is zero.

14. The valve assembly of claim 7, wherein the valve housing, flow channel, and valve shaft are part of a mechanically operated needle valve.

15. The valve assembly of claim 7, wherein the flow selector comprises a rotatable knob, such that rotation of the rotatable knob causes a rotation of the valve shaft.

16. The valve assembly of claim 7, wherein the flow selector comprises a rotatable flow selector,
wherein the valve assembly further comprises an engagement cavity in the rotatable flow selector configured to receive the first end of the valve shaft,
wherein the rotatable flow selector is configured to remain in a fixed position axially with respect to the valve housing, and
wherein the valve shaft is free to translate axially within the engagement cavity while remaining engaged with the engagement cavity.

17. A method for controlling the flow rate of a fluid within a valve assembly, comprising:
defining a flow channel in a valve housing to allow a fluid to flow from an input to an output;
rotationally securing a valve shaft within the flow channel, such that rotation of the valve shaft causes a first end of the valve shaft to translate within the flow channel to control a flow rate of the fluid from the input to the output;
rotationally securing a second end of the valve shaft to a flow selector;
indicating, via an axially fixed valve stop plunger, the relative location of the valve shaft with respect to the flow channel, wherein the valve stop plunger is configured be plunged by moving tangentially with respect to the rotation of the valve shaft by an actuator associated with the valve shaft as the valve shaft is axially translated, wherein the actuator is configured to rotate with the valve shaft; and
detecting, via a position detector, when the valve stop plunger is plunged to a position indicating that the valve shaft is axially translated such that the flow rate of the fluid from the input to the output corresponds to a threshold flow rate.

18. The method of claim 17, wherein the actuator associated with the valve shaft protrusion on the valve shaft.

19. The method of claim 18, wherein the protrusion is mechanically coupled to the valve shaft.

20. The method of claim 17 wherein the actuator comprises a cam configured to move the valve stop plunger relative to the position detector based on the relative axial location of the valve shaft with respect to the flow channel.

21. The method of claim 17, wherein the threshold flow rate corresponds to a minimum safe flow rate of a medically required gas, such that the flow rate of the fluid from the input to the output is the minimum safe flow rate of the medically required gas.

22. The method of claim 21, wherein the medically required gas comprises oxygen and the minimum safe flow rate is between 1 liter per minute and 2 liters per minute.

23. The method of claim 17, wherein the threshold flow rate corresponds to zero, such that the flow rate of the fluid from the input to the output is zero.

24. The method of claim 17, wherein the valve housing, flow channel, and valve shaft are part of a mechanically operated needle valve.

25. The method of claim 17, wherein the rotatable flow selector is configured to remain in a fixed position axially with respect to the valve housing, and
    wherein the valve shaft is free to axially translate within the engagement cavity while remaining engaged with the engagement cavity.

\* \* \* \* \*